(12) United States Patent  
Braun et al.

(10) Patent No.: US 8,574,258 B2  
(45) Date of Patent: Nov. 5, 2013

(54) OCCLUSION DEVICE AND METHOD OF USE

(75) Inventors: Michael Braun, Backnag (DE); John S. Geis, Bad Zwischenahn (DE); Brian M. Strauss, Irvine, CA (US); Jay A. Lenker, Laguna Beach, CA (US)

(73) Assignee: Reverse Medical Corporation, Irvine, CA (US)

( * ) Notice: Subject to any disclaimer, the term of this patent is extended or adjusted under 35 U.S.C. 154(b) by 147 days.

(21) Appl. No.: 12/936,666

(22) PCT Filed: Apr. 8, 2009

(86) PCT No.: PCT/US2009/039967
§ 371 (c)(1),
(2), (4) Date: Aug. 22, 2011

(87) PCT Pub. No.: WO2009/126747
PCT Pub. Date: Oct. 15, 2009

(65) Prior Publication Data
US 2012/0022572 A1    Jan. 26, 2012

Related U.S. Application Data

(63) Continuation-in-part of application No. 12/024,974, filed on Feb. 1, 2008, now Pat. No. 8,333,783.

(60) Provisional application No. 61/043,233, filed on Apr. 8, 2008, provisional application No. 60/890,340, filed on Feb. 16, 2007.

(51) Int. Cl.
*A61M 29/00* (2006.01)

(52) U.S. Cl.
USPC .......................................... 606/198

(58) Field of Classification Search
USPC ............... 604/96.01, 101.01–101.03, 101.05, 604/104–109; 606/159, 194, 198, 200; 623/1.11, 1.12, 1.23
See application file for complete search history.

(56) References Cited

U.S. PATENT DOCUMENTS 6,902,540 B2 * 6/2005 Dorros et al. ............... 604/8
2002/0026210 A1 * 2/2002 Abdel-Gawwad .......... 606/194

(Continued)

OTHER PUBLICATIONS

PCT International Search Report, International Application PCT/US2009/039967 (Jul. 10, 2009).

(Continued)

*Primary Examiner* — Ryan Severson
*Assistant Examiner* — Katherine M Shi
(74) *Attorney, Agent, or Firm* — K. David Crockett, Esq.; Crockett & Crockett, PC

(57) ABSTRACT

A device for protecting cerebral vessels or brain tissue during treatment of a carotid vessel includes a catheter having a distal portion, a proximal portion and a lumen extending therebetween, the catheter including first and second expandable areas provided over the length of the catheter. The device includes a first elongate member insertable longitudinally through the lumen of the catheter, the first elongate member being configured for stretching at least a portion of the catheter and causing one of the first and second expandable areas to transition from an expanded state to a collapsed state. The device further includes a second elongate member insertable longitudinally through the lumen of the catheter, the second elongate member being configured for stretching at least a portion of the catheter and causing the other of the first and second expandable areas to transition from an expanded state to a collapsed state.

14 Claims, 21 Drawing Sheets

(56) References Cited

U.S. PATENT DOCUMENTS

| | | |
|---|---|---|
| 2005/0197693 A1 | 9/2005 | Pai et al. |
| 2006/0200191 A1 | 9/2006 | Zadno-Azizi |
| 2007/0027518 A1 | 2/2007 | Case et al. |
| 2008/0045881 A1 | 2/2008 | Teitelbaum |
| 2008/0065008 A1 | 3/2008 | Barbut et al. |

OTHER PUBLICATIONS

PCT IPRP and Written Opinion, International Application PCT/US2009/039967 (Oct. 12, 2010).

* cited by examiner

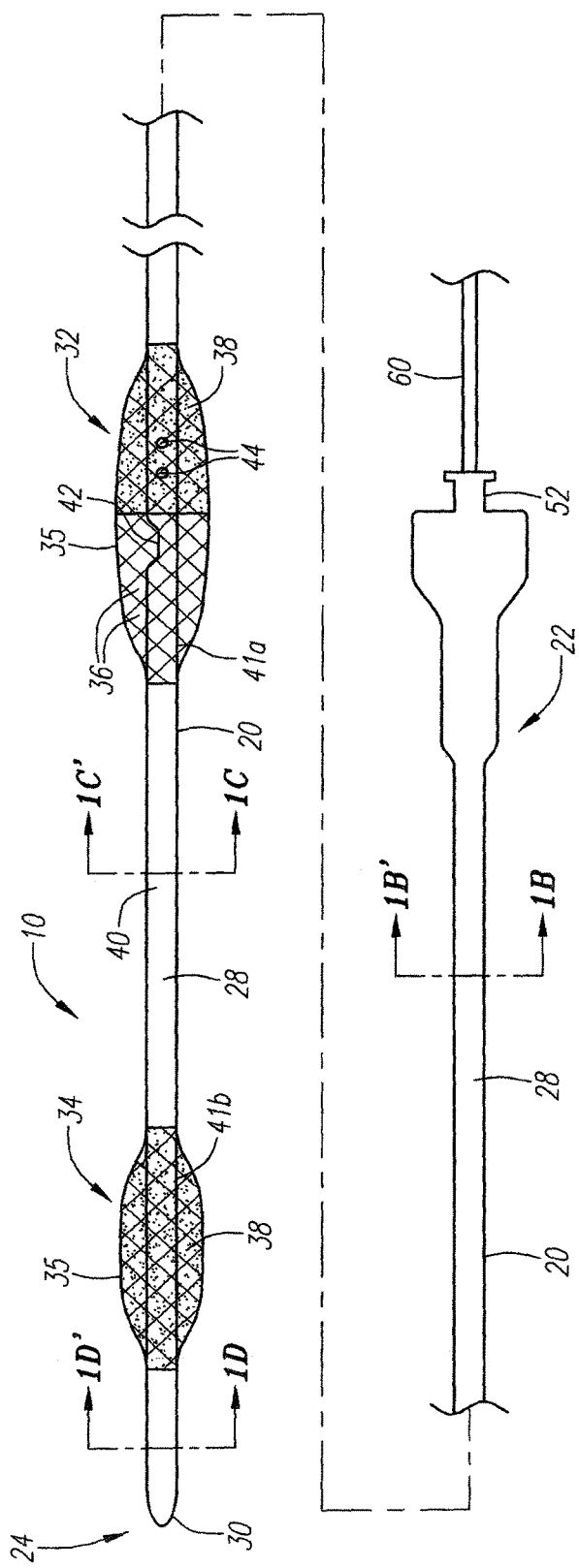
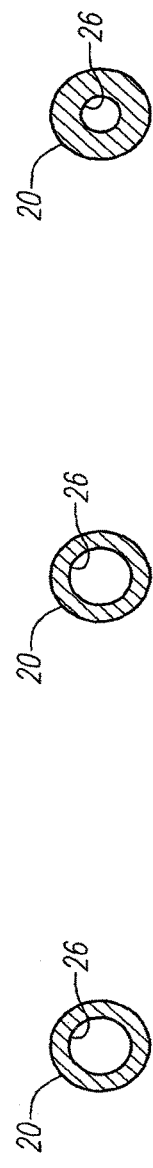
FIG. 1A
FIG. 1B    FIG. 1C    FIG. 1D

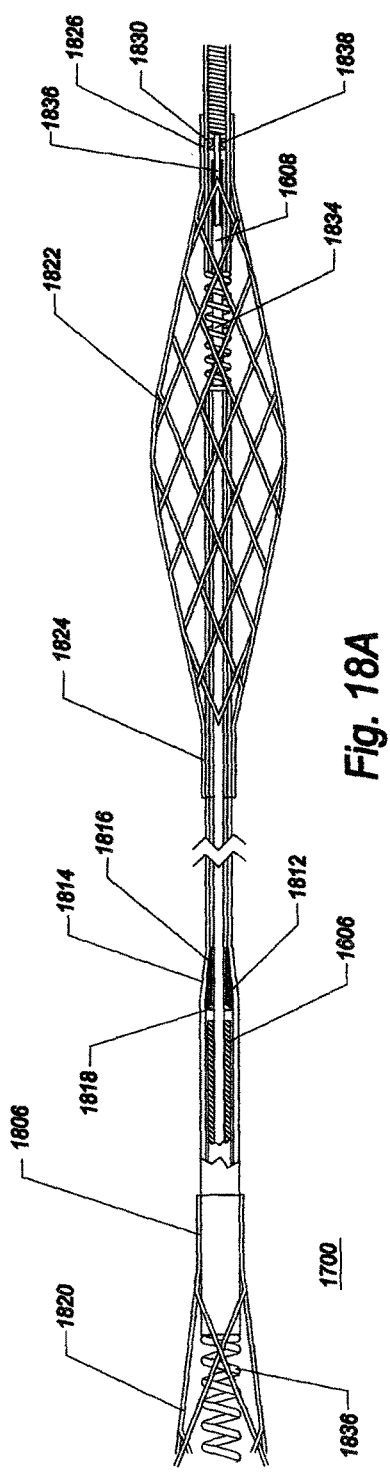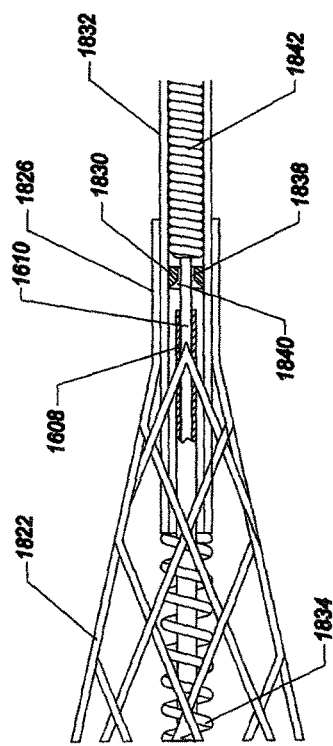
Fig. 18A
Fig. 18B

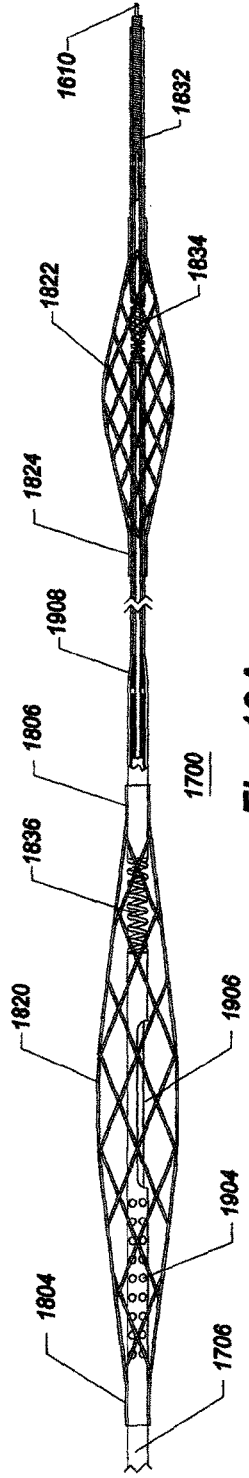
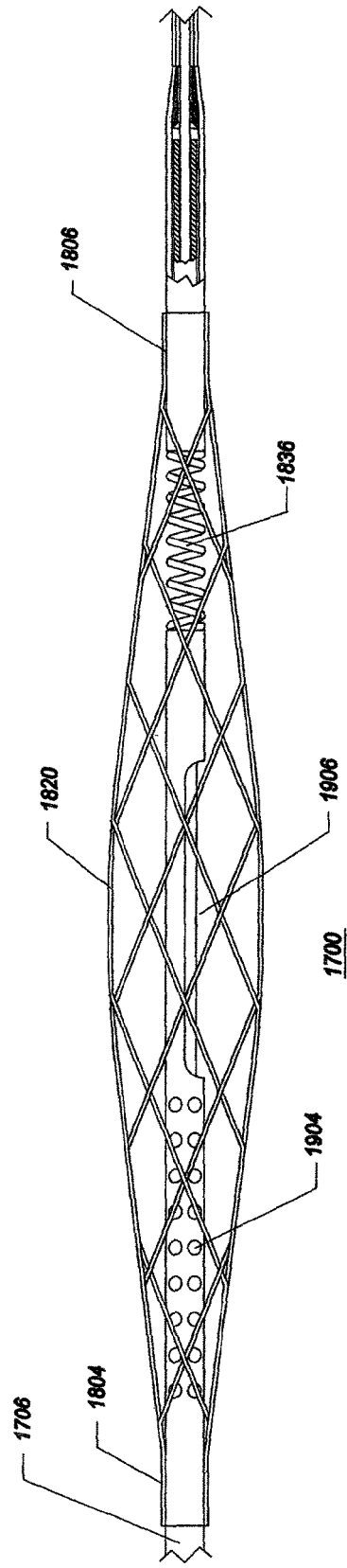

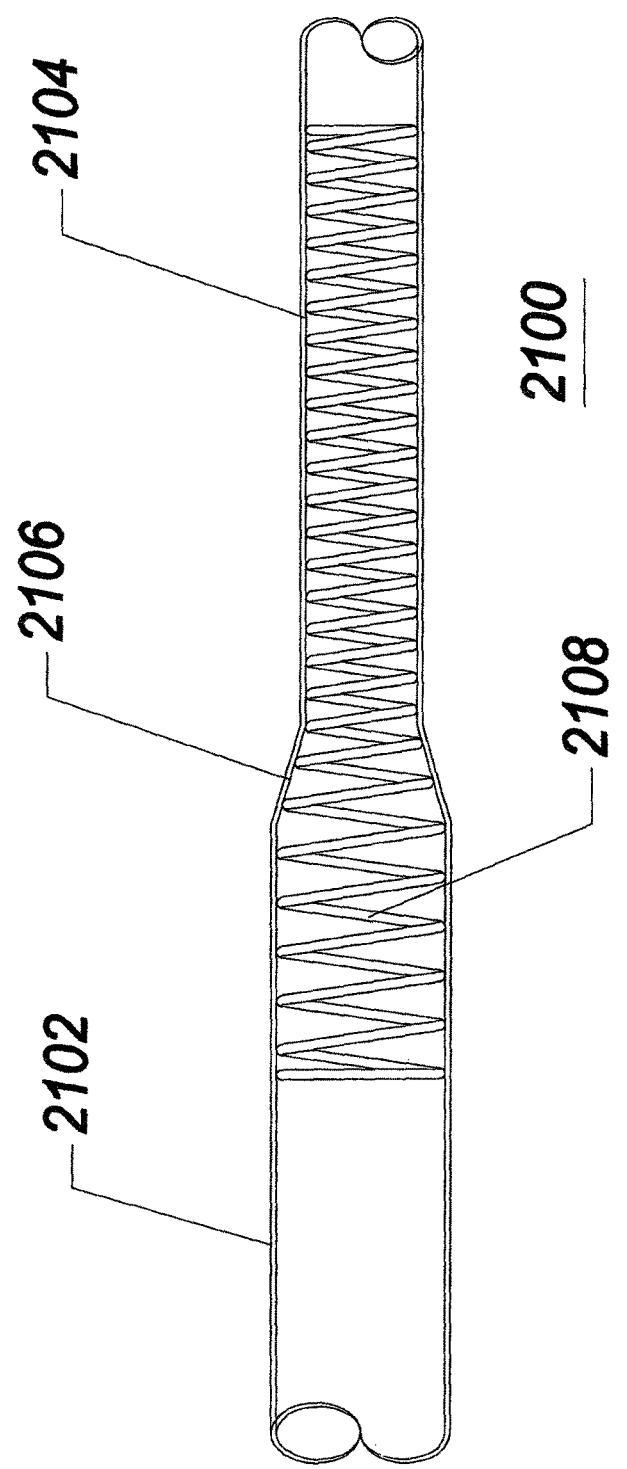

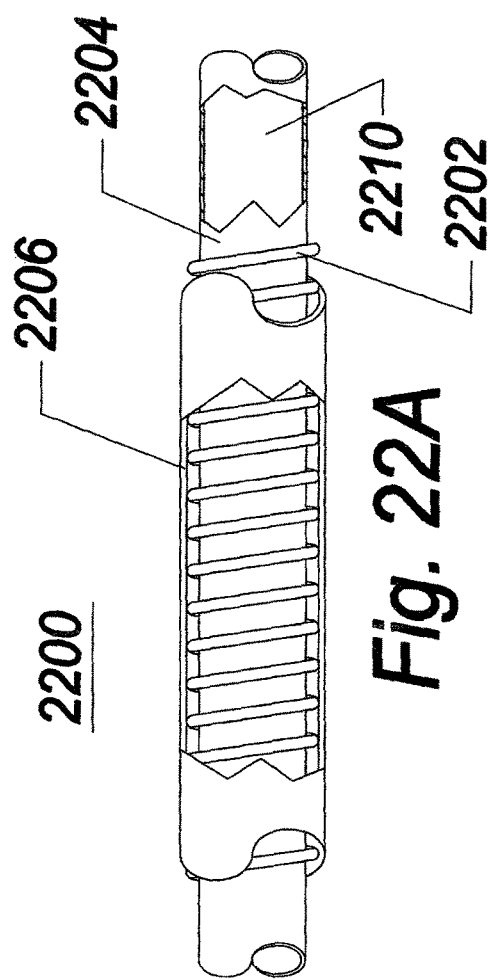
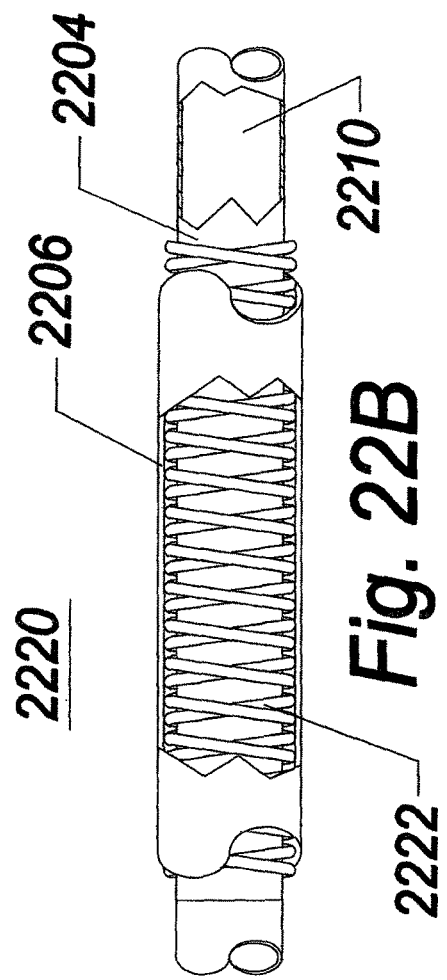

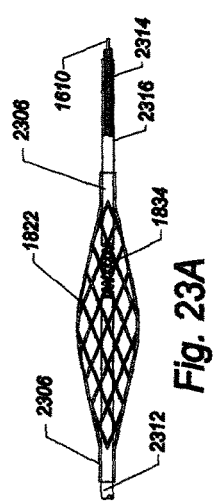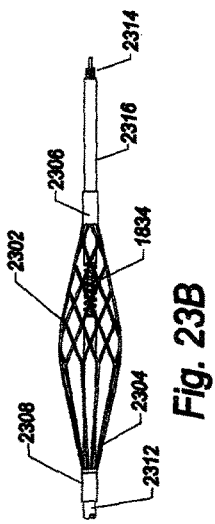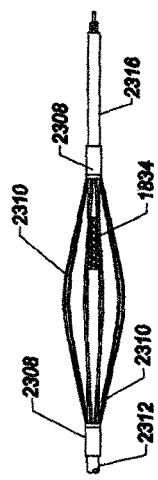

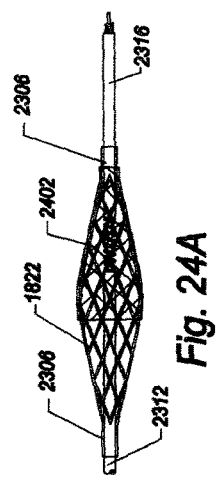 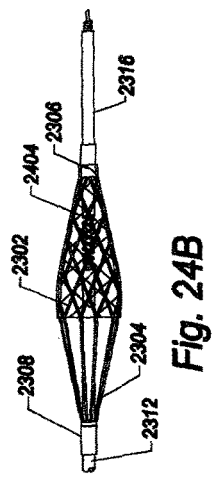 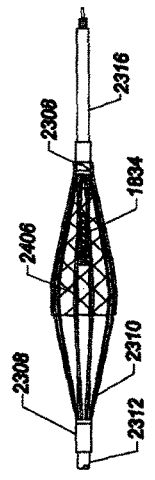

US 8,574,258 B2

OCCLUSION DEVICE AND METHOD OF USE

REFERENCE TO RELATED APPLICATIONS

This application claims priority to U.S. Provisional Patent Application Ser. No. 61/043,233 filed Apr. 8, 2008, the entire disclosure of which is expressly incorporated herein by reference. Additionally, this application is a continuation in part of copending U.S. patent application Ser. No. 12/024,974, filed on Feb. 1, 2008, which claims priority to U.S. Provisional Patent Application No. 60/890,340 filed on Feb. 16, 2007 pursuant to 35 U.S.C. §119, the entire disclosures of which are expressly incorporated herein by reference.

FIELD OF THE INVENTION

The field of the invention generally relates to devices and methods for protecting cerebral vessels and brain tissue during treatment of the carotid vessels. More particularly, the field of the invention pertains to devices and methods for inducing retrograde flow within the carotid vessels so as to eliminate the migration of particulate matter in the direction of normal cerebral blood flow.

BACKGROUND OF THE INVENTION

In the case of stenosis in the carotid artery, atherosclerotic plaques are present at the vessel wall of the external carotid artery, the internal carotid artery, or the common carotid artery. These plaques have to be removed as they hinder the blood flow. A number of catheter-based angioplasty procedures as well as various surgical and non-surgical procedures have been developed for this reason. There is, however, a risk with these procedures, whereby parts of the plaque or other material may loosen and be released as emboli into the blood stream. In particular, such released particles can migrate in the direction toward the cerebral blood vessels due to the antegrade (i.e., forward moving) blood flow. The emboli have a high probability of becoming lodged within the cerebrovasculature causing flow blockage, brain tissue ischemia, and cell death. This represents a major risk for the patient. Vessel filters, which are supposed to block micro and macro-sized particles, have been developed in order to minimize or avoid these risks.

Conventional filter devices are disadvantageous in that they have to be positioned in a distal position relative to the stenosis in order to catch the released or sloughed off particles, which, according to the natural antegrade blood flow, would be transported towards the cerebral brain tissues and ultimately the brain. These vessel filters thus have to be guided beyond the stenosis before they can be deployed. Unfortunately, the process of guiding the filter through the area of the stenosis may itself result in the dislodging of particulate matter, which then may lead to emboli.

A so-called proximal protection system has been suggested as an additional protection against such risks. This system uses the selective placement of two inflatable balloons to effect retrograde blood flow (i.e., a reversal of the blood flow direction). For example, the MO.MA cerebral protection device developed by Invatec (Italy) operates on this principal. In the MO.MA system a catheter device includes two inflatable balloons, which serve to occlude the suitable vessels and generate a reverse blood flow. In this design, the main catheter is essentially a balloon catheter having two inflation lumens that communicate with the two inflatable balloons. A working lumen is provided in the catheter where an external instrument can be guided to treat the stenosis.

Another system developed by W.L. Gore & Associates, Inc. (GORE Neuro Protection System) utilizes a catheter having an inner lumen along with a distally located inflatable balloon sheath. A separate balloon wire is guided within the inner lumen of the catheter. The balloon wire is advanced into the external carotid artery (if the stenosis is present in the internal carotid artery) and the balloon is expanded to occlude the external carotid artery. Antegrade blood flow in the direction of the external carotid artery will thereby be stopped. The second inflatable balloon sheath, which is positioned at the distal end of the balloon catheter, is then inflated to occlude the common carotid artery. The blood flow of the common carotid artery will thus be stopped. Flow reversal is achieved at the treatment site by selective occlusion of the external carotid artery and the common carotid artery. Blood that tries to flow from the internal carotid artery to the common carotid artery will be hindered by the balloon sheath of the balloon catheter and instead is guided into the lumen of the balloon catheter for filtration and subsequent redirection into the patient via venous return. A working device such as a dilation balloon catheter, which is necessary for the further dilation of the stenosis, is guided within the balloon catheter lumen.

By inducing retrograde blood flow, the above-mentioned systems can potentially avoid a migration of particles in the direction of the cerebral blood vessels. Also, a penetration of the area of the stenosis is not necessary. The above-noted systems are, however, disadvantageous because they require relatively large dimensions. In particular, the inner diameter of the balloon catheter has to be large due to the various system components to be guided therein (e.g., external balloon and other intervention tools). In addition, the incorporation of the inflation lumen(s) into the catheter makes for devices having larger diameters and reduced space available for the working lumen. This is a particular concern because the sizes of the therapeutic and diagnostic tools for carotid artery intervention are constrained due to the limited space available within the balloon catheter. It may not be possible to adapt the size of the intervention tools to the required small size.

There thus is a need for improved methods and devices for occluding one or move vessels to protect cerebral vessels and the brain. For instance, there is a need to have occlusion devices that have a relatively low profile (e.g., outer diameter). Smaller devices are more manageable to handle at the vascular access site (e.g., femoral artery) and offer additional flexibility through the tortuous vascular anatomy. There is a need for an occlusion device that is easier to use than the devices described above. For example, the GORE Neuro Protection System uses separate elongate devices having inflatable balloons thereon. A single device that incorporates both proximal and distal occlusive elements is easier to use. In addition, an occlusion device should be able to be used with a single guidewire that can be used for protection device deployment as well as delivery of a working instrument such as a stent or balloon catheter.

Additionally, there is a need for a device that incorporates a single step to deploy the proximal and distal occlusion elements. For example, in the MO.MA cerebral protection device, two separate inflation lumens (one for proximal balloon and one for distal balloon) must be actuated for full deployment of the occlusive balloons. For full deployment of the balloons in the GORE Neuro Protection device, as explained above, the user must inflate the balloon wire in addition to the separate balloon sheath located on the distal end of the catheter. In addition, it would be preferably to provide a device having occlusive elements that do not need the cumbersome and space-occupying inflation lumens used in balloon-based devices. The device should also have the ability to rapidly re-establish normal or antegrade flow given the potential for occlusion intolerance in the patient. Finally, the device should offer near constant procedural imaging capability.

SUMMARY OF THE INVENTION

The present invention provides devices and methods for treating disorders in blood vessels and other luminal structures of a human or animal body.

In accordance with one aspect of the present invention, there is provided a device which comprises: a catheter having a distal portion, a proximal portion and at least one lumen extending therebetween, the catheter including first and second expandable areas; a first elongate member insertable through a lumen of the catheter so as to cause expansion of at least a portion of the catheter and transitioning of one of the first and second expandable areas from an expanded state to a collapsed state and a second elongate member insertable through a lumen of the catheter so as to cause expansion of at least a portion of the catheter and transitioning of the other one of the first and second expandable areas from an expanded state to a collapsed state. Following insertion of the first elongate member, such first elongate member may be retractable proximally relative to the catheter to cause the one of the first and second expandable areas to transition from a collapsed state to an expanded state. Also, following insertion of the second elongate member, the second elongate member may be retractable proximally relative to the catheter to cause the other of the first and second expandable areas to transition from a collapsed state to an expanded state. In some embodiments, the first and/or second elongate members may comprise elongate stretching members, stylets or pusher members.

In accordance with another aspect of the present invention, there is provided a device that comprises a catheter having a distal portion, a proximal portion, a lumen and an expandable area, said expandable area including a length changing region disposed at least partially within the expandable area; and an elongate member moveable within a lumen of the catheter and connected to a distal end of the expandable area such that application of proximally-directed force to the elongate member causes the expandable area to expand and application of a distally directed force to the elongate member causes the expandable area to collapse.

Further in accordance with another aspect of the present invention, there is provided a method for treating a vessel that is bifurcated into two branches, such method generally comprising the steps of: (A) providing a catheter having first and second expandable areas; (B) inserting a first elongate member so as to cause the expandable area to be in a collapsed state; (C) inserting a second elongate member so as to cause the second expandable area to be in a collapsed state; (D) inserting the catheter into the vessel such that the first expandable area is distal to a bifurcation of the vessel in one of the branches and the second expandable area is proximal to the bifurcation; (E) retracting the first elongate member to allow the first expandable area to expand; and (F) retracting the second elongate member to allow the second expandable area to expand.

Still further in accordance with another aspect of the invention, there is provided a device for protecting cerebral vessels or brain tissue during treatment of carotid vessels includes a catheter having a distal portion, a proximal portion, and lumen extending therebetween. The catheter includes first and second expandable areas for vessel occlusion that are provided over a length of the catheter. In another embodiment, the catheter can comprise more than two expandable areas. The device includes a removable elongate member that is insertable longitudinally through the lumen of the catheter. The elongate member is configured for stretching at least a portion of the catheter and causing the first and second expandable areas to transition from an expanded state to a collapsed state. When the elongate member is retracted proximally relatively to the catheter, the first and second expandable areas transition from the collapsed state to an expanded state. In one aspect of the invention, the expandable areas expand at substantially the same time. The collapsed state refers to a state wherein the expandable area comprises a first, smaller diameter, radius, or cross-sectional configuration. The expanded state refers to a state wherein the expandable area comprises a second, larger diameter, radius, or cross-sectional configuration.

The expandable areas can be formed from self-expandable members disposed along the length of the catheter or they can be areas of the catheter body itself that are forced by a separate component of the expandable area to expand. Expandable areas are regions of the catheter, which assume the expanded state due to changes of external influences and maintain the expanded state without further influence from the outside. The expansion generally occurs in the radial direction of the longitudinal axis of the catheter. The change of external influences can, for example, be the removal of a mechanical or magnetic force being imposed onto the area or a change in temperature. The lateral cross-sectional configuration of the expandable areas in the expanded state can comprise shapes including but not limited to spherical, elliptical, oblong, or cylindrical. In the collapsed or stretched state, the expandable areas can assume the shape of a cylinder or tube and preferably have an outer diameter corresponding substantially to the outer diameter of the catheter tube or body on/in which these areas are provided.

The device allows for the occlusion of two vessels, and in particular, vessels having a bifurcation area from which extends a plurality of branches or vessels. For example, the device can be used in the external carotid artery and the common carotid artery to treat a stenosis located in the internal carotid artery. In contrast to balloon catheter-based devices, occlusion can be accomplished without necessitating the usage of devices, tools, or fluids that have to remain in the catheter of the device during the intervention. Because of this, the lumen of the catheter can serve as a guide for other instruments necessary for the intervention, such as interventional tools. This results in a catheter that has a relatively small outside diameter, e.g., about 7.5 French or less.

The elongate member can have the shape of a catheter, a rod, a wire, or the like and can be guided within the lumen of the catheter of the device. By advancing the elongate member axially in the distal direction within the catheter until it abuts a stop or receiving member operatively coupled to the catheter and then applying distal, axial force against the stop, a stretching of the first and second expandable areas in an axial direction of the catheter is accomplished which results in a reversal of the radial expansion (e.g., collapsed state). If the elongate member is retracted proximally within the lumen of the catheter, the force imposed in the axial direction of the catheter is reduced and the self-expandable areas can naturally expand in the radial direction. Expansion in the radial direction also causes the length of the expandable areas to reduce or foreshorten. As the elongate member can be removed from the catheter, the lumen of the catheter will be available for other usages, such, as the insertion of one or more intervention tools. Another advantage of deploying the expandable areas by proximal retraction of the elongate member is that the expandable areas, preferably two expandable areas, can be expanded substantially simultaneously. This means that the time for generating a blood flow desirable for the proximal protection during treatment of the carotid vessels is minimal, as the occlusion of the respective vessels can be generated in one rapid step.

In some embodiments one or both of the elongate members may have a lumen, for example a lumen dimensioned for passage of a guidewire. A guidewire having a diameter of about 0.010 to 0.017 inches, and preferably about 0.013 to 0.015 inches is suitable for this purpose. The inner lumen can be configured to slidably accept such a guidewire by making the inner lumen diameter approximately 0.001 to 0.005 inches larger than that of the guidewire. This makes it possible to securely advance the elongate member in an over-the-wire manner. The elongate member can, for example, be a catheter or a hypotube. A hypotube is a hollow metal tube of very small diameter. These tubes, which are, inter alia, used for manufacturing hypodermic needles, have a longitudinal stiffness (high column strength) and a small wall thickness.

In another aspect of the invention, in the vicinity of the distal end of the inner lumen of the catheter, a receiving member is provided for receiving the distal tip of the elongate member. The receiving member can be a tapered distal end of the inner lumen of the catheter. According to one embodiment, the receiving member extends proximally from the distal end of the inner lumen to at least the distal end of the expandable area provided nearest the distal end of the catheter (i.e., "the distal expandable area"). The receiving member can beneficially comprise an inner diameter that is tapered inwardly moving from the proximal to distal direction on the inner lumen of the catheter. Because the elongate member that is inserted into the inner lumen of the catheter mainly serves the purpose of applying a force in the longitudinal direction towards the distal end of the catheter and thereby collapsing the expandable areas to the collapsed or non expanded state, it is sufficient to provide a receiving member for the elongate member at the distal end of the distal expandable area. The distal tip of the catheter beyond the distal end of the distal expandable area can thus optionally be solid with only a lumen dimensioned for slideable passage of the guidewire (but not the elongate member). In this way, a contact, abutment, or stopping face for the distal end of the elongate member is provided and yet the catheter can still be inserted over a guidewire. For example, a 0.015 inch diameter inner lumen would pass a 0.014 inch diameter guidewire but not a 0.016 inch diameter member.

According to another embodiment, the receiving member extends from the distal end of the inner lumen to at or near the proximal end of a distal expandable area, preferably to the proximal end of the distal expandable area in its expanded state. In this alternative embodiment, the receiving member can be a rod, tube, or channel with a lumen dimensioned for passage of the guidewire. The rod, tube, or channel can be attached at the distal end of the catheter, i.e. only on the distal end of the rod, tube, or channel. Alternatively or additionally, the rod, tube, or channel can be attached at its outer diameter to the inner surface of the inner lumen of the catheter between the distal end of the distal expandable area and the distal end of the catheter.

By providing a receiving member that extends through the distal expandable area, the introduction of the elongate member later during the intervention may be facilitated. As will be described later on in detail, the guidewire that is used for initial placement of the catheter can be withdrawn proximally from the distal end of the catheter. In this situation, an advancing of the elongate member without the presence of the guidewire will be guided by the inner lumen of the catheter. In the region of the expandable area, however, an inner tubular shaped lumen may not be present. Because of this, the guiding of the elongate member to the distal end of the inner lumen of the catheter may be difficult. By providing a receiving member extending to the proximal end of the distal expandable area, such a penetration of the elongate member through the expandable area is not necessary. In addition, the overall distance over which the elongate member has to be advanced to reach a position where the longitudinal stretching force can be applied to the catheter is reduced.

The receiving member can include or comprise a recess (e.g., an angled or tapered) at its proximal end for facilitating the receipt of the distal end of the elongate member. The distal end of the elongate member can have a profile that matches or mates with the recess of the receiving member. The recess can have, for instance, a cone shape to receive a tapered distal end of the elongate member.

In another aspect of the invention, at least one expandable area of the catheter can include an inner and an outer component. The inner or outer component, or parts thereof, can be part of the catheter wall or body. If the inner component forms part of the catheter wall, it preferably only extends over part of the length of the expandable area. The remaining length of the inner component can be formed by a flexible member such as an elastic sheath. If the inner component is formed at least partially by the catheter material, the outer component can be a self-expandable element. The self-expandable element can be a braid, a mesh, a knit, a net, or the like. The proximal end of the self-expandable element can be attached to the outside of the catheter wall proximal to the portion of the catheter wall formed to which the flexible member (e.g., an elastic sheath) can be attached. The distal end of the self-expandable element can be attached to a proximal end of the catheter wall, which is attached to the distal end of the flexible member. In this case the self-expandable element can take the form of a tubular member (e.g., tube or the like). The outer component of the expandable area is radially self-expandable and preferably in a normal or expanded state in the absence of the presence of the elongate member.

Alternatively or additionally, the inner component is a contraction member for axially contracting the expandable area. In this case, the inner component can be a spring, in particular a helical spring. The outer component of the expandable area of this embodiment can be the catheter wall or catheter body or a self-expandable element. If the outer catheter is formed by the catheter wall, one or more slits or other openings can be provided to allow radial expansion or buckling of the catheter wall in this area. If the outer component is a self-expandable element it can comprise a braid, mesh or a net.

Another alternative for actuating (e.g., expanding) the expandable areas can be due to a contraction force applied by an outer component or coating. In this case, a coating is provided over at least part of the expandable areas and induces an axially-oriented contraction force. In order to achieve such a contraction, the material such as a braid, net or mesh is covered in a state of maximal radial expansion, i.e. is covered, when it is axially compressed to the desired deployment diameter (e.g., ~20 mm for the proximal expandable area). When coating at least a part of the area in this axially compressed (and thus radially expanded state), the axial distance between adjacent elements, e.g. struts, is fixed by the coating. The coating material is preferably elastic material, such as silicone, polyurethane, or PTFE. If an expandable area at least partially coated with such coating is axially stretched and the stretching force is removed, the expandable area will return to the radially expanded state due to the contracting force applied by the coating on adjacent elements, such as struts.

Preferably, at least one of the expandable areas has openings in at least part of the expandable area. By providing openings, e.g. mesh openings, blood and particulate matter can enter into the inner volume of the expandable area and can be guided from there, for example via one or more holes, passageways, or ports in the inner component of the expandable area into the inner lumen of the catheter from where it can be transported to appropriate treatments, such as filters located external to the patient. Of course, the holes, passageways, or ports can also be located in other portion(s) of the catheter besides the inner component.

For filtering the collected blood and other fluid, the proximal end of the inner lumen of the catheter is at least temporarily connected to a collecting device, such as a container or bag and a filter can be provided at the inlet of the collecting device. The blood removed together with particles from the vessel can thus be separated from the particles and may be re-introduced into the body of the patient at a later stage.

In one aspect of the invention, the openings in the expandable area can additionally serve for permitting the passage of one or more intervention tools. Interventional tools can include, for example, a balloon catheter, stent catheter, or the like. If an inner component is provided in the expandable area, the inner component can also be provided with a respective opening.

In at least one of the first and second expandable areas, an outer component of the expandable area is preferably formed by a mesh, a net, a knit, or a braid. This embodiment is advantageous in that a homogeneous expansion of the expandable area can be ensured. In addition, the mesh, net, or braid structure also provides the holes or passageways through which fluid may flow so that the same can be directed proximally out of the catheter. In one aspect, the material being used for the self-expandable areas is made of a shape memory material. This can include a metal alloy such as, for instance, NITINOL. Alternatively, a spring material can be used to form the self-expandable areas.

According to one embodiment, in the proximally located expandable area, the size of the openings in the distal portion of the expandable area is larger than the size of the openings in the proximal portion of the expandable area. For example, the size of openings at the distal portion of the expandable area can be in the range of about 0.5 mm to about 5.0 mm and the size of the openings in the proximal portion can be smaller than about 1 mm. The distribution of sizes of the openings is preferable because, in one aspect, the proximal portion of the expandable area can be provided with a coating or cover while the distal portion can be left uncovered and can thus let blood and particles as well as intervention tools pass.

As explained above, at least a portion of the expandable areas can be partially or fully covered or coated in order to be able to use areas made of braid, mesh, or netting for occlusion of the blood vessel(s) of interest. The coating or covering is formed on or over the braid, mesh, or netting and closes the openings of the respective areas and prevents penetration of liquids, in particular of blood so as to form a substantially leak-free seal between the expandable area and the interior of the vessel.

According to one aspect, the proximally located self-expandable area is at least partially covered at the proximal end. For example, only about half of the length of the proximal expandable area (i.e., the proximal half), is covered. The distal portion of the proximally located self-expandable area is uncovered. The distally located, self-expandable area can be covered partially or completely.

The proximally located self-expandable area and the distally located self-expandable area can have the same or different sizes upon deployment. In one aspect, the distally located self-expandable area has a smaller diameter in the expanded state than the proximally located, self-expandable area in the expanded state.

According to one embodiment, the catheter is provided with at least one aperture in the catheter located between proximal end of the most proximal expandable area and the proximal end of the most distal expandable area. The at least one aperture can be provided between the two expandable areas or in the proximal expandable area. This aperture can be positioned on the side of the catheter tube or wall and can be generated by, for example, drilling, scraping, or cutting off the material of the catheter over a given length. The aperture offers the ability to bring intervention tools from within the lumen of the catheter to the site of intervention within the blood vessel without having to remove the catheter. The aperture offers a side port or access passageway for additional therapeutic devices. For example, the aperture allows the same catheter used to establish retrograde blood flow to also be used as the catheter for interventional tools, such as a balloon catheter or guidewire. The aperture can thus be provided in the wall of the catheter tube and/or within the expandable area and is dimensioned to allow passage of an intervention tool, e.g. a balloon catheter, therethrough.

It is desirable to allow for smooth guidance of the elongate member and/or an intervention tool through and past an expandable area particularly when it is in its expanded state. Guiding can be provided by an inner component of the expandable area, such as a spring or part of the catheter tube and/or an elastic membrane. In particular, insertion through the proximal expandable area when expanded benefits from such an interior guide.

The interior guide, can for example, be formed by a flexible membrane sheath formed using, for example, an elastic material, which extends over at least part of the length of the expandable area. The interior guide can also, at least partially, be formed by a portion of the catheter tube or body. The length of the portion of the catheter tube extending into the expandable area should be dimensioned so that this portion of the catheter tube does not abut to the other end of the catheter tube on the other side of the expandable area when the area assumes the expanded state. In one aspect, the interior guide preferably has at least one hole or orifice that is in fluid communication with the lumen of the catheter. The at least one hole or orifice serves for removal of blood together with possibly particles into the catheter. In the case of a spring as being used as the inner component of the expandable area, the holes or orifices are formed by the distance between the spiral windings.

According to a further aspect of the present invention, a method for treating a vessel having a bifurcation area from which extends a plurality of branches includes inserting a catheter with at least two self-expandable areas for occlusion of vessels provided over the length of the catheter into a vessel, while an elongate member is inserted within the lumen of the catheter to keep the expandable areas in a collapsed state. A distal expandable area is positioned distal to the bifurcation of the vessel in one of the branches, thereby positioning a proximal expandable area proximal to the bifurcation of the vessel. Upon retracting the elongate member, the at least two expandable areas are urged to expand. The elongate member can have a longitudinal stiffness greater than that of the first and second self-expandable areas.

While positioning the distal expandable area in one branch of the bifurcation an aperture can be positioned at or near the bifurcation. The aperture allows the passage of one or more intervention tools out through the catheter. The aperture can be located between the distal and proximal expandable area or in the proximal expandable area. For guiding the catheter to the intended position, a guidewire is normally inserted into the vessel before the insertion of the catheter and the elongate member. In this regards, both the catheter and the elongate member can be advanced in an over-the-wire arrangement.

After the removal of the elongate member from the lumen of the catheter, the distal end of the guidewire will be retracted proximally until it reaches an aperture of the catheter distal to the proximal end of the proximally located self-expandable area and is advanced distally through the aperture into the other branch of the bifurcation. Thereby the guidewire will be brought into a position for guiding intervention tools such as a balloon catheter or balloon catheter. Consequently, it is not necessary to remove the guidewire completely from the catheter to introduce a different device. The exchange of the elongate member and the intervention tool can be a rapid "over-the-wire" exchange. The distance over which a guidewire has to be advanced from the point of entry to the location of treatment is considerable, in particular for treatments of carotid vessels, where the devices will typically be inserted via the femoral artery. By avoiding the retraction and exchange of guidewires, the intervention time can be reduced considerably.

The distally located self-expandable area occludes the vessel of a branch distal to the branching position and blood flow is directed from the other branch toward the proximal expandable area in a retrograde manner. Preferably, the proximally located self-expandable area occludes the blood vessel proximal to the bifurcation and the blood flow passes through one or more openings provided in the proximally-locate self-expandable area into an interior portion of the self-expandable area. The blood flow then continues into the lumen of the catheter via one or more openings provided in the catheter or interior guide located within the proximally located self-expandable area. According to one embodiment, a medical instrument, e.g. a balloon catheter, balloon wire, or balloon catheter is inserted via the proximal end of the lumen of the catheter and guided to an aperture provided within the catheter wall. The medical instrument is inserted over the guidewire, and is guided out of the aperture and into the branch vessel to be treated.

In some embodiments, the distal expandable region can be made to expand and contract separately from the proximal region. Such a device having separate proximal and distal expansion regions can comprise a plurality of stylets having different diameters to selectively engage the proximal expandable region or the distal expandable region. The plurality of stylets can be separately inserted into the proximal end of the catheter or they can be coaxially disposed within the catheter so that, for example, the smaller central stylet controls the distal expandable region while the larger diameter outer stylet controls the expansion of the proximal expandable region. Alternatively, a stylet split down the approximate middle and with one side capable of sliding axially relative to the other side can be used to separately actuate the proximal and distal expandable regions. In yet another embodiment, the radial expansion can be generated using magnetic coupling between a control device and the proximal or distal expandable region.

In other embodiments, the expandable regions can comprise longitudinally disposed bars, struts, or wires. In a further embodiment, the longitudinally disposed bars, struts, or wires can be malleable or resilient/elastomeric. Upon application of a proximally directed force on the distal end of the bars, the longitudinal bars bend radially outward, while application of distally directed force on the distal end of the bars causes the bars contract radially inward. Bar construction using malleable materials allows for a Moly-bolt design that maintains its shape following removal of the proximally or distally directed axial force. In another embodiment, the expandable regions can comprise metal braid. In another embodiment, the expandable regions can comprise polymeric braid fabricated from materials such as PET, polyimide, PEN, and the like. In another embodiment, the expandable regions can comprise a braid for part of its structure and longitudinal struts for the rest of its structure. For example, the distal expandable region can comprise braided metal wire in its approximately distal ½ length and metal longitudinal struts in its proximal ½ length. In an embodiment, the braided region can be further closed with a finely woven, knitted, or braided basket or it can enclose or be coated with a polymeric film.

The system can comprise radiopacity enhancements to improve visualization under fluoroscopy. In an embodiment, the distal, fixed guidewire can be fabricated from platinum, a radiodense material. In another embodiment, the distal, fixed guidewire can be fabricated from stainless steel, which is then coated with platinum, gold, tantalum, or the like. The stainless steel construction enhances the strength of the coil while the coatings, although thin, improve the radiopacity of the object being coated.

In certain embodiments, the inner member, the innermost catheter tube to which the distal expandable member is affixed at its distal end, can be fabricated using a reinforcement of coil, braid, or the like. The coil or reinforcing braid can be fabricated from stainless steel, titanium, Nitinol, cobalt nickel alloy, or the like. The coil is preferably elastomeric with good spring properties and does not exhibit malleable tendencies. The spacing between the coils can, for example range from substantially 0 to approximately 4 times the width of the coil wire. The coils can be fabricated from round stock, flat stock, or the like. The reinforcement can be sandwiched between an inner layer and an outer layer of polymeric material, wherein the inner and outer layers can be bonded or welded to each other through the space between the coils. The inner and outer polymeric layers can be fabricated from the same or different materials. Suitable materials for the inner and outer layers include, but are not limited to, polyurethane, silicone, Hytrel, PEEK, polyethylene, HDPE, LDPE, polyester, and the like.

In certain embodiments, the aspiration holes on the inner member can have an aggregate cross-sectional area that is equal to or greater than the cross-sectional area of the lumen of the inner member. In these embodiments, the aspiration holes do not impose a substantial restriction on the fluid being injected or withdrawn through the inner member lumen.

In certain embodiments, the catheter shaft can comprise multiple regions of varying flexibility along the axial length of the shaft. In some embodiments, the catheter shaft can have at least two regions of different flexibility. In other embodiments, the catheter shaft can comprise three or more (with a practical upper limit of six) regions of different flexibility. In yet other embodiments, the catheter shaft flexibility can be reduced toward the proximal end of the catheter and increased moving toward the distal end of the catheter. Moving from the proximal to the distal end of the catheter shaft, the flexibility of a given discreet section can be greater than the flexibility of the region just proximal and adjacent to said discreet section.

In certain embodiments, the inner member can comprise snake cuts to increase the flexibility of the inner member in the region of the snake cuts. Snake cuts can include cuts into the inner member, wherein the cuts are laterally directed and positioned in the same circumferential location but at different axial locations. The laterally directed cuts do not penetrate entirely through the diameter of the catheter so that a spine or backbone can exist around which the inner member can flex in a single two dimensional plane. In another embodiment, the number of snake cuts per unit length can vary to fine tune the flexibility of the device. In yet other embodiments, a portion of the snake cuts can be made at a circumferential location different from that of other snake cuts. Thus, the catheter shaft can flex within the aforementioned two dimensional plane as well as a second two dimensional plane, wherein the second plane can be advantageously aligned approximately orthogonal to that of the first plane.

In other embodiments, the pusher can also have a plurality of different flexible regions. These flexible regions on the pusher can be created using coil reinforced composite pusher construction, braid reinforced composite pusher construction, slotted pusher construction, or the like.

In yet other embodiments, the outer member can be constructed of composite materials having reinforced intermediate structures such as, but not limited to, perforated metal tubes, coils, braided metals or polymers, or the like. The interior and the exterior surfaces of the outer member can be fabricated from polymeric materials such as, but not limited to, polyethylene, PEEK, polypropylene, Hytrel, pebax, polyurethane, silicone elastomer, thermoplastic elastomer, or the like.

In some embodiments, the outer member can have a thin wall, ranging from about 0.008 inches or 0.20 mm up to 0.020 inches or 0.50 mm.

In yet other embodiments, the outer member can comprise a continuous winding through the taper and flexible guide tip. The winding can be routed all or part of the way across the tapered region by using a tapered winding mandrel and a compensating feed on the coil winding machine. In certain embodiments, the continuous winding can be fabricated from round, flat, or oval wire composed of stainless steel. The taper is located near, and preferably distal to, the distal end of the proximal expandable region. The winding can comprise a gap in the coils proximal to the taper. The winding can comprise no space between the coils approximately distal to the taper. The diameter of the outer member can range from about 4 mm to about 10 mm and preferably between 5 mm and 8 mm. The winding can be routed part way, or all the way out to the distal end of the flexible tip for simplicity of manufacture.

For purposes of summarizing the invention, certain aspects, advantages and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein. These and other objects and advantages of the present invention will be more apparent from the following description taken in conjunction with the accompanying drawings.

BRIEF DESCRIPTION OF THE DRAWINGS

A general architecture that implements the various features of the invention will now be described with reference to the drawings. The drawings and the associated descriptions are provided to illustrate embodiments of the invention and not to limit the scope of the invention. Throughout the drawings, reference numbers are re-used to indicate correspondence between referenced elements.

FIG. 1A illustrates a side view of a catheter according to one aspect of the invention.

FIG. 1B illustrates a cross-sectional view of the catheter of FIG. 1A taken along the line B-B'.

FIG. 1C illustrates a cross-sectional view of the catheter of FIG. 1A taken along the line C-C'.

FIG. 1D illustrates a cross-sectional view of the catheter of FIG. 1A taken along the line D-D'.

FIG. 2A illustrates the proximal and distal self-expandable areas in the collapsed state.

FIG. 13 illustrates the proximal and distal self-expandable areas in the collapsed configuration after the elongate member has been re-introduced over the guidewire.

FIG. 18A illustrates a central region of a flow reversal embolic protection catheter configured to engage the two-stage pusher.

FIG. 18B illustrates an expanded view of the region where the smaller diameter portion of the two-stage pusher engages the flow reversal embolic protection catheter.

FIG. 19A illustrates the central region of FIG. 18A slightly expanded to show more of the proximal expandable mesh and the complete distal tip of the flow reversal embolic protection catheter.

FIG. 19B illustrates an enlarged view of the region encompassing the proximal expandable mesh.

FIG. 21 illustrates an embodiment of a step-down in a catheter shaft whereby a coil reinforcement is disposed across the step-down or transition zone.

FIG. 22A illustrates a length of axially elongate tubing fabricated in layers and comprising an intermediate reinforcing coil, an inner layer, and an outer layer.

FIG. 22B illustrates a length of axially elongate tubing 2220 fabricated in layers and comprising an intermediate reinforcing braid 2222, an outer layer, and an inner layer.

FIG. 23A illustrates a side view of a radially expandable region comprising a radially expandable mesh and a length adjustable region on the catheter tubing within the mesh.

FIG. 23B illustrates a side view of a radially expandable region comprising a radially expandable mesh at one end of the expandable region, a plurality of struts at the other end of the expandable region, and a length adjusting region on the catheter tubing within the radially expandable region.

FIG. 23C illustrates a side view of a radially expandable region comprising a plurality of struts that span the entire radially expandable region and a length adjusting region on the catheter tubing within the expandable region.

FIG. 24A illustrates a side view of a radially expandable region comprising a radially expandable mesh and a membrane covering the distal aspect of the mesh.

FIG. 24B illustrates a side view of a radially expandable region comprising a radially expandable mesh at one end of the expandable region, a plurality of struts at the other end of the expandable region, and a membrane covering the mesh on the distal end of the expandable region.

FIG. 24C illustrates a side view of a radially expandable region comprising a plurality of struts that span the entire radially expandable region and a membrane covering the distal end of the struts.

DETAILED DESCRIPTION OF THE ILLUSTRATED EMBODIMENTS

Figure 2A:
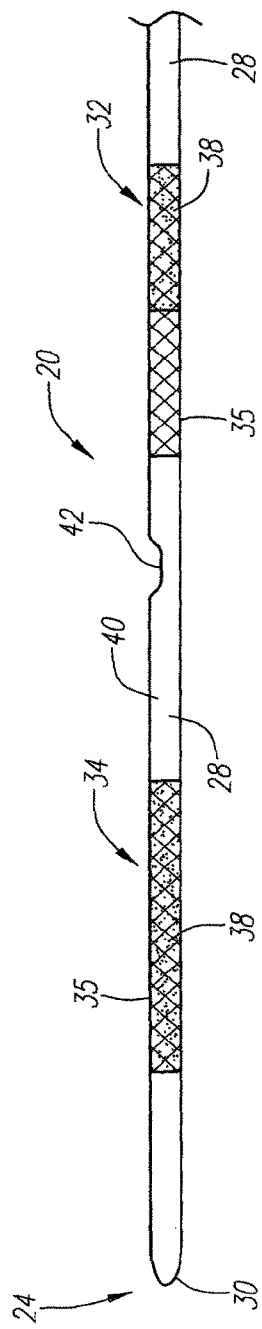
FIG. 2A is a side view of a catheter according to one embodiment.

As used herein, the terms proximal and distal refer to a direction or a position along a longitudinal axis of a catheter or medical instrument. Proximal refers to the end of the catheter or medical instrument closest to the operator, while distal refers to the end of the catheter or medical instrument closest to the patient. For example, a first point is proximal to a second point if it is closer to the operator end of the catheter or medical instrument than the second point.

FIGS. 1A-1D, 2A-2C, 3A, 3B, and 4 illustrate various aspects of a system 10 for the protection of cerebral vessels or brain tissue. The system 10 includes a catheter 20 (illustrated in FIGS. 1A-1D), an elongate member 60 which, in this embodiment functions as an elongate member (illustrated in FIGS. 1A, 3A and 3B), and a guidewire 80 (illustrated in FIG. 4). The system 10 can also include one or more additional components used during the interventional procedure. These include, for instance, an introducer or the like (not shown) that is used during introduction and placement of the catheter 20.

Referring to FIGS. 1A-1D, the catheter 20 is formed as an elongate member having a proximal end 22 and a distal end 24 and a lumen 26 extending therebetween. The catheter 20 includes an elongate body portion 28 that can incorporate a coiled and/or braided structure, or reinforcement, to impart sufficient axial compressive strength while at the same time providing the capability of the catheter 20 to bend through tortuous regions of the vasculature. In one aspect, the outer diameter of the catheter 20 is between about 3 French (F) to a maximal 10 F. However, in another aspect of the invention, the diameter falls within this range, for instance, the outer diameter ranging from between 4 F and 7 F. The length of the catheter 20 can be between about 60 cm and about 145 cm, with a preferable range between about 90 cm and 120 cm, although other lengths are contemplated to fall within the scope of the invention. As explained herein, one of the advantages of the system 10 is the ability to produce a very small device having a diminished size as compared to other devices.

In one embodiment, the lumen 26 extends fully from the proximal end 22 to the distal end 24. The lumen 26 can have varying or differing internal diameters depending on the particular location within the catheter 20. For example, as seen in FIGS. 1B and 1C, the diameter in the main body portion 28 of the catheter 20 can be substantially constant. In this portion, the diameter of the lumen 26 is generally determined by the dimensions of the interventional tool(s) being used and by the outer diameter of the catheter. Nonetheless, the inner diameter of the lumen 26 in this region generally falls within the range of about 3 F to about 7 F. In another aspect of the invention, the inner diameter of the lumen 26 in this region generally falls within the range of about 4 F to about 6 F. However, in one aspect of the invention, near the distal end 24 of the catheter 20 the diameter of the lumen 26 is reduced as illustrated in FIG. 1D. The diameter of the lumen 26 near the distal end 24 of the catheter 20 is dimensioned so as to permit passage of a guidewire 80 but not permit passage of the elongate flexible member 60. For example, the reduced diameter lumen 26 at or near the distal end 24 can have an inner diameter within the range of about 0.010 to 0.030 inches and preferably between 0.012 and 0.020 inches. In a preferred embodiment, for example, the reduced inside diameter of the lumen 26 near the distal end can be about 0.016 inches. Thus, a commonly used 0.014 inch diameter guidewire will pass through the lumen 26 and extend out the distal end 24 of the catheter 20, whereas an elongate member 60 having a diameter of 0.024 inches will not pass through the distal, reduced diameter portion of the lumen 26.

Figure 8:
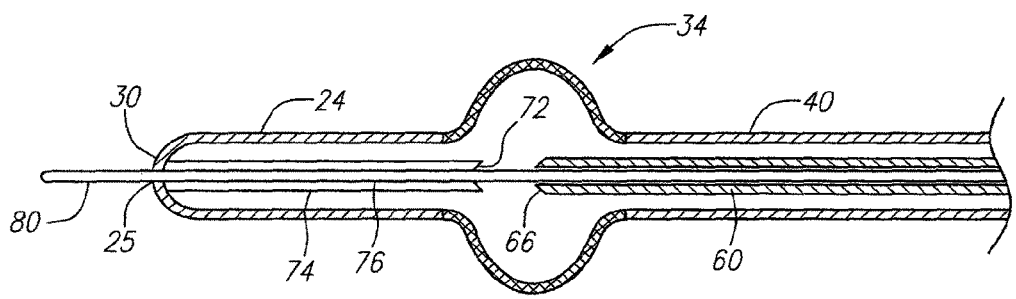
FIG. 8 illustrates a cross-sectional view of the distal end of a catheter according to another embodiment. The elongate member and guidewire are illustrated therein.

Some, or all, of the inner surface of the lumen 26 may be coated or formed with a lubricious coating to improve the slidability of the elongate member 60 or working instruments within the lumen 26 during use of the system 10. Of course, all or portions of the elongate member 60 can optionally be coated with a lubricious coating such as coatings fabricated from polyurethane, silicone oil, other hydrophilic materials, or the like. In certain embodiments, the hydrophilic lubricious coating bond to the catheter 20 can be enhanced by plasma discharge treatment to roughen the surface of the catheter 20 and increase mechanical bond strength. Such plasma discharge treatment can be beneficial when the catheter 20 is fabricated from materials, such as polyethylene, polypropylene, polyester, polytetrafluoroethylene, and the like, that do not bond well to other materials. Referring to FIG. 1A and FIG. 8, the distal end 24 of the catheter can terminate in an atraumatic tip 30 that includes an opening 25 therein for passage of the guidewire 80. As seen in FIG. 1A, the catheter 20 is interrupted at two locations. At each interruption location is located a self-expandable area 32, 34. One self-expandable area is deemed a proximally located self expandable area 32 while the other self-expandable area is located distally with respect thereto and is deemed a distally located self-expandable area 34. Both self-expandable areas 32, 34 are configured to transition between a collapsed state and an expanded state. The interrupted areas are configured to permit longitudinal or axial movement of the distal ends of the self-expandable areas 32, 34, relative to the proximal ends of the self-expandable areas 32, 34. The collapsed state refers to a state in which the expandable areas 32, 34 comprise a minimum radius, diameter, or cross-sectional area. In the collapsed state, the self-expandable areas 32, 34 are substantially flush with the outer diameter of the catheter 20. In this regard, in the collapsed state, the self-expandable areas 32, 34 generally take a tubular-shaped configuration. FIG. 1A illustrates both self-expandable areas 32, 34 in a partially collapsed state so as to better illustrate various aspects of the system 10. Each expandable area 32 and 34 comprises a proximal end and distal end, which is affixed to the catheter shaft 20. The proximal end and the distal end of the expandable areas 32, 34 can be bonded, welded, or mechanically fixed to the catheter shaft 20.

In the expanded state, as described below, the self-expandable areas 32, 34 foreshorten along the longitudinal direction of the catheter 20 and form a spherical, elliptical, oblong, or cylindrical shape. The shape of the self-expandable areas 32, 34 is, however, not limited to the depicted shapes. The distal self-expandable area 34 can also, for example, have a cylinder shape, the shape of a funnel, a bowl, or of a plate. The deciding issue when choosing a particular deployment shape is that it is suitable for completely occluding the blood vessel, i.e. stop the blood flow, in the state, where the self-expandable area 32, 34 is expanded within the blood vessel. The perimeter of a partially, or fully, expanded self expandable area 32, 34 can be round or it can comprise a noncircular shape that conforms to an irregular vessel wall inner contour. Also the shape of the proximal self-expandable area 32 in the expanded state can be different from the depicted shape. For example, the proximal self-expandable area 32 area can have the shape of a sphere, an umbrella, or a plate. With the proximal self-expandable area 32 it is important that it is capable of occluding the blood vessel between the catheter 20 and the vessel wall in its expanded state. The proximal end and the distal ends of the expandable areas 32, 34 do not change their diameter even when the expandable areas 32, 34 are expanded and thus appear as tapered end regions on the expandable areas 32, 34.

In one aspect of the invention, the self-expandable areas 32, 34 are formed from a shape memory material. For example, the self-expandable areas 32, 34 can be formed from a shape memory alloy or metal such as NITINOL or other spring material such as stainless steel, cobalt nickel alloy, titanium, and the like. The self-expandable areas 32, 34 can be formed from a plastic or polymer such as polyester. The two self-expandable areas 32, 34 can be made of the same or, alternatively, different materials. In an embodiment where the self-expandable areas 32, 34 comprise NITINOL, the NITINOL can be superelastic or pseudoelastic in nature. In this embodiment, the austenite finish temperature is well below body temperature or even room temperature, causing the self expandable areas 32, 34 to possess strongly biased spring tendencies to expand laterally or radially outward from the longitudinal axis of the catheter 20.

In another embodiment, the self-expandable areas 32, 34 comprise shape-memory NITINOL, which has an austenite finish temperature above room temperature. In a preferred embodiment, the austenite finish temperature of the final self-expandable areas 32, 34 ranges between 25 to 35° C. and preferably between 28 and 33° C. In yet another embodiment, the self-expandable areas 32, 34 comprise shape memory NITINOL having an austenite finish temperature above body temperature such that external energy can be imparted to the self-expandable areas 32, 34 to generate the desired expansion. Such external energy can be in the form of Ohmic, or resistive, heating generated by electricity delivered through wires traversing the length of the catheter 20. Alternatively the energy can be imparted using methodologies such as, but not limited to, microwaves, radio-frequency energy, a hot balloon, high intensity focused ultrasound, and the like.

Figure 12:
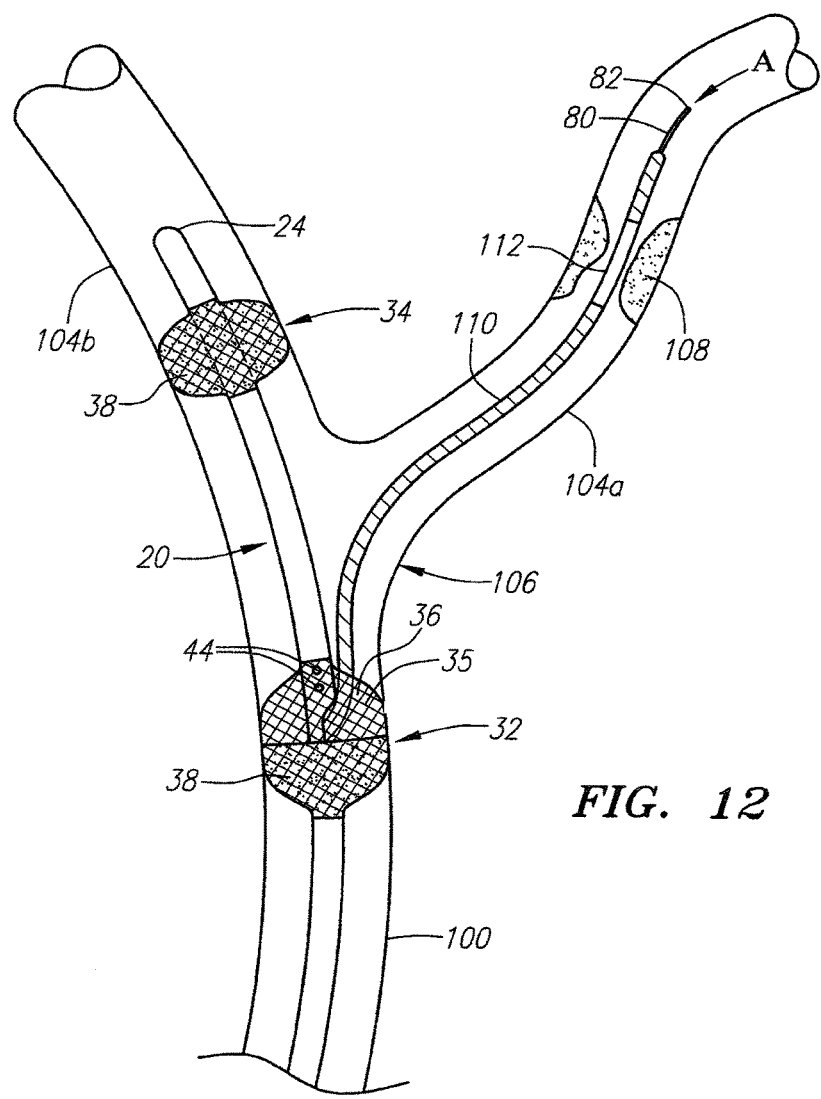
FIG. 12 illustrates the catheter of FIG. 11 with a working instrument being advanced over the guidewire for treatment of the stenosis.

The self-expandable areas 32, 34 can be configured as a mesh 35 as depicted in FIG. 1A. Of course, other configurations such as a braid, knit, weave, or netting can be used for the self-expandable areas 32, 34. As illustrated in FIG. 1A, at least a portion of the proximally located self-expandable area 32 includes a number of openings 36 located in the mesh 35. The openings 36 provide access for blood and potential particulate matter and other fluid to pass through during use of the system 10. The openings 36 can also be dimensioned to pass the guidewire 80 and interventional tool 110 as illustrated in FIG. 12. The mesh 35 (or other configuration) may have openings 36 that are regularly spaced and substantially uniform in size. Alternatively, the particular pattern or configuration of the openings may be varied or irregular. For example, with respect to the proximal self-expandable area 32, the distal portion of the mesh 35 may have larger cell openings 36 to better facilitate passage of the working instrument 110.

In one aspect of the invention, a portion of the proximally located self-expandable area 32 includes a cover 38. For example, the proximal portion of the self-expandable area 32 in FIG. 12 includes the cover 38 while the distal portion of the self-expandable area 32 is uncovered, thereby exposing the mesh 35 and openings 36 to the external environment. In one aspect, substantially the proximal half of the self-expandable area 32 is surrounded by the cover 38. In one embodiment, the distally located self-expandable area 34 can be fully covered by the cover 38. In another embodiment, however, only a distal portion of the distally located self-expandable area 34 can be surrounded by or enclosed by the cover 38. The cover 38 can be fabricated from a biocompatible flexible material that is substantially impermeable to fluids. Examples of materials suitable for use as the cover 38 include, but are not limited to, polytetrafluoroethylene, polyurethane, Hytrel, polyethylene, polyester, polyamide, polyimide, thermoplastic elastomer, silicone elastomer, and the like. The cover 38 can be separately manufactured and adhered or otherwise affixed to the mesh 35 on either the inside or the outside of the mesh 35. Alternatively, the cover 38 can be created by dipping, spraying, or other known applications. In this regard, the cover 38 can actually be a coating that is formed directly on the mesh 35. The cover 38 may be formed an interior surface of the mesh 35 or, alternatively, on an exterior surface of the mesh 35. The cover 38 can be manufactured as a fabric by weaving, braiding, knitting, or the like. In yet another embodiment, the fabric cover 38 can be coated with a polymeric coating or membrane as described above. The cover 38 can be affixed to the mesh 35 by adhesive bonding, welding, coating, attachment with mechanical fasteners, or the like.

In another embodiment, the portion of the self-expandable areas 32, 34 which are covered or otherwise coated with the cover 38 can be less than half of the length of the self-expandable areas 32, 34. The cover 38 only has to extend far enough to ensure the sealing or occluding of the end face formed in the expanded state between the catheter body 28 and the vessel wall, where this area abuts. The distal self-expandable area 34 can also only be partially covered although FIG. 1A illustrates a fully covered distal self-expandable area 34. For example, the distal portion of the self-expandable area 34 may be covered leaving the proximal portion uncovered. Alternatively, the entire distal self-expandable area 34 may be coated except for a plurality of filling holes that permit fluid passage to an interior portion. Also, here it should be ensured that the entire diameter of the blood vessel, into which the self-expandable area 34 is inserted, is covered to the inside of the vessel. A cover 38 or coating of only the upper or lower half can thus be sufficient to achieve full occlusion.

The size and ultimate shape of the self-expandable areas 32, 34 depend on the particular vessel(s) being treated. For example, the proximally located self-expandable area 32 may have a diameter of about 20 mm when expanded and may have a length of less than about 5 cm in the collapsed state. The distally located expandable area 34 can have a diameter of about 15 mm when expanded and can have a length of less than 3 cm in the collapsed state. In the collapsed state, both the proximal and distal self-expandable areas 32, 34 have outer diameters which substantially correspond to the outer diameter of the catheter 20 for a flush configuration. In addition, in the collapsed state, the length of the proximally located self-expandable area 32 is larger than the length of the distal self-expandable area 34. Of course, the dimensions described above are illustrative examples and diameters and lengths falling outside this ranges described above are contemplated to fall within the scope of the invention.

Still referring to FIG. 1A, the proximal and distal self-expandable areas 32, 34 are separated by an intermediate potion 40, which is formed by the body portion 28 of the catheter 20. The intermediate portion 40 thus separates the two self-expandable areas 32, 34. The length of the intermediate portion 40 can fall within the range of about 2 cm to about 15 cm or within a narrower range of about 5 cm to about 10 cm. As seen in FIG. 1A, the self-expandable areas 32, 24 include a hollow inner flexible member 41a, 41b disposed radially inward of the self-expandable mesh 35. For example, in the proximally located self-expandable area 32, the flexible member 41a is secured at one end to the intermediate portion 40 of the catheter and at the other end to the catheter body 28 which partially extends into the self-expandable area 32. The distally located flexible member 41b is secured at one end to the intermediate portion 40 and at the other end to the distal end 24 of the catheter 20.

The flexible members 41a, 41b can be formed from a membrane material or flexible tube having a lumen therein that is configured to permit passage of the elongate member 60. The flexible members 41a, 41b are what enable the catheter 20 to lengthen when the elongate member 60 is advanced within the lumen 26 of the catheter 20 to apply a tensioning force along the length of the catheter 20. The flexible members 41a, 41b serve as interior guides 48, 50, respectively, for the proximal and distal self-expandable areas 32, 34. The flexible members 41a, 41b can be secured to the outer mesh 35 instead of to the catheter 20 body.

Still referring to FIG. 1A, the catheter body 28 extends somewhat into the proximally located self-expandable area 32. An aperture 42 is provided that communicates with the lumen 26 of the catheter 26. The aperture 42 can be formed by scraping or cutting off the material of the catheter 26 over a given length to form a skived aperture 42. The aperture 42 is dimensioned to allow passage of one or more working instruments such as, for instance, a guidewire 80 and balloon catheter. The aperture 42 can be oriented or positioned adjacent to an uncovered portion of the mesh 35 in the proximally located expandable area 32. In this regard, the guidewire 80 and/or balloon catheter can be advanced along the main lumen 26 and out the aperture 42 so as to position the guidewire 80 and/or balloon catheter through the openings 36 in the mesh 35 and external to the device.

Figure 2B:
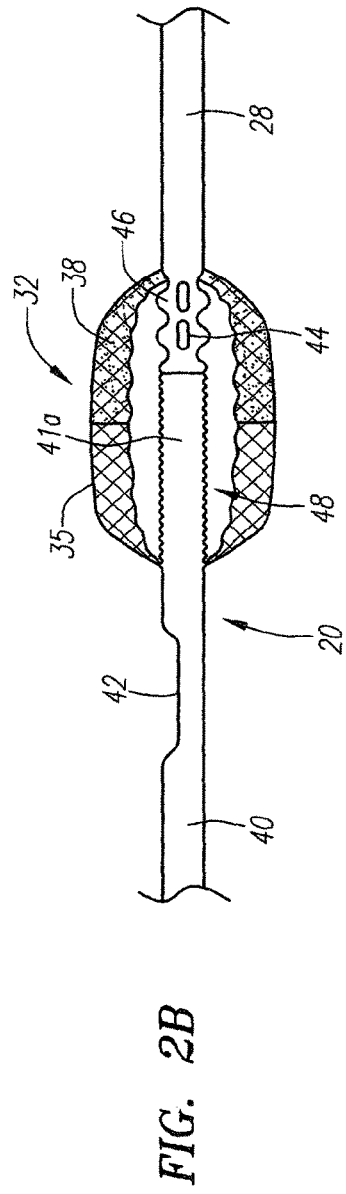
FIG. 2B illustrates a partially cut-way view of the proximal self-expandable area according to one embodiment.
Figure 2C:
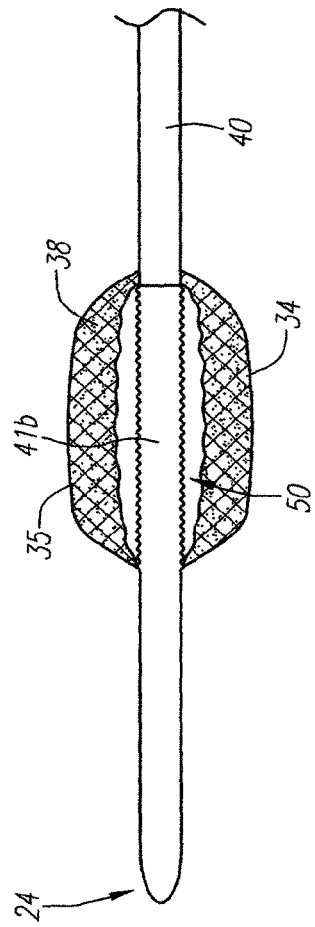
FIG. 2C illustrates a partially cut-way view of the proximal self-expandable area according to another embodiment.

FIGS. 2A and 2B illustrate another embodiment of the catheter 20 in which the aperture 42 is located in the intermediate portion 40 between the proximal and distal self-expandable areas 32, 24. The aperture 42 extends over a given amount in the longitudinal direction of the catheter 20. The aperture 42 can also be configured to straddle a portion of the proximally located self-expandable area 32. In FIG. 2A, both self-expandable areas 32, 24 are illustrated in a collapsed state wherein their outer diameters are substantially equal to the outer diameter of the catheter 20. FIG. 2B illustrates a cut-away view of the internal aspect of the proximally located self-expandable area 32. In this embodiment, the catheter body 28 extends over the proximal end of the self-expandable area 32 and into the self-expandable area 32 to form part of an interior guide 48. In the portion 46 of the catheter body 28 that extends into the self-expandable area 32, a plurality of holes 44 are disposed that provide access to the interior lumen 26. At the end of the catheter portion 46, a flexible member 41a in the form of a membrane sheath is attached. In the depicted embodiment, the membrane sheath 41a extends to the distal end of the proximal self-expandable area 32. There the membrane sheath 41a can be attached to the catheter body 28, which forms the intermediate area 40. Alternatively, the membrane sheath 41a can be attached to the material (e.g., mesh 35), which forms outer component of the self-expandable area 32. A similar interior guide 50 can be located within the distally located self-expandable area 34 as illustrated in FIG. 2C. This particular interior guide 50 can have a similar layout as the interior guide 48 within the proximal self-expandable area with the exception that there are no openings in the catheter body 28 extending into the distal self-expandable area 34.

Referring back to FIG. 1A, one or more holes 44 are provided in the catheter 20 to provide an access pathway to inside the lumen 26 of the catheter 20. The holes 44 can be disposed inside the proximally located self-expandable area 32. Blood with potential particulate matter is able to flow into the lumen 26 of the catheter 20 via the access holes 44 which can be populated about the periphery of the catheter 20. FIG. 2B illustrates an alternative embodiment of the catheter 20 illustrating the plurality of holes 44 disposed within the interior guide 48 portion. Generally, the holes or orifices 44 may be located in the most proximate portion of the self-expandable area 32 so as to prevent the accumulation of debris proximate to the holes 44. The holes or orifices 44 may be populated around the periphery of the catheter 20. The number of holes or orifices 44 and their diameters is such that the combined cross-sectional area of all the holes 44 is at least as great as the cross-sectional area of the lumen 26 of the catheter 20.

Figure 3A:
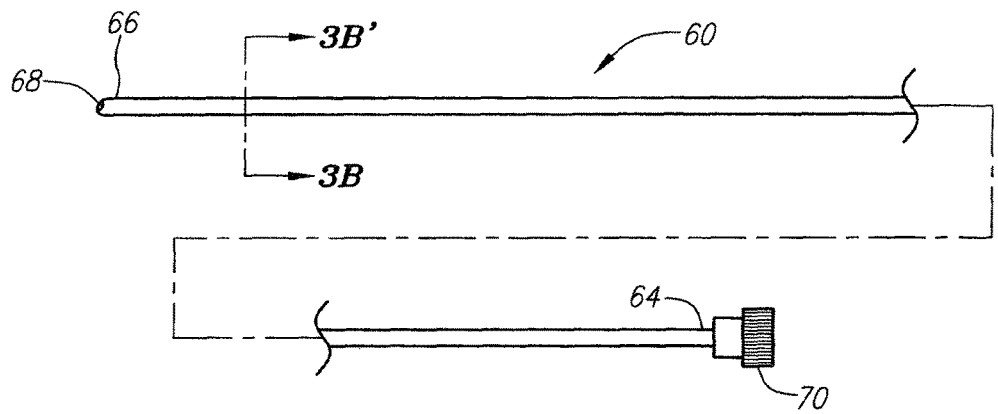
FIG. 3A illustrates an elongate member according to one embodiment of the invention.
Figure 3B:
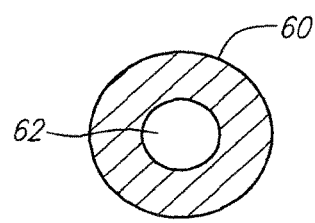
FIG. 3B illustrates a cross-sectional view of the elongate member taken along the line B-B' of FIG. 3A.

FIGS. 1A, 3A, and 3B illustrate an elongate member 60 that is used as part of the system 10. The elongate member 60 is an elongate member that is configured to slide within with lumen 26 of the catheter 20. In this regard, the elongate member 60 is removable from within the catheter 20 to selectively expand or contract the self-expandable areas 32, 34 based on the presence or absence within the lumen 26. The elongate member 60 includes a lumen 62 (shown in FIG. 3B) that is configured to receive a guidewire 80 as explained in more detail below. The lumen 62 preferably traverses the entire length of the elongate member 60 from a proximal end 64 to a distal end 66. The distal end 66 of the elongate member 60 advantageously includes a hole 68 located at or near the tip such that the guidewire 80 can pass for deployment of the system 10. The proximal end 64 of the elongate member 60 includes a locking member 70 that is configured to mate with a proximal hub 52 of the catheter 20.

The locking member 70 is advantageously located a fixed distance away from the distal end 66 such that when the elongate member 60 is fully inserted into the lumen 26 of the catheter 20 and the proximal and distal self-expandable areas 32, 34 are collapsed as shown in FIG. 2A, the locking member 70 is able to be secured to the proximal hub 52. In this regard, the locking member 70 secures or otherwise locks the relative position between the catheter 20 and elongate member 60 to maintain the first and second self-expandable areas 32, 34 in the tensioned, collapsed state. The locking member 70 can be secured to the proximal hub 52 via threads or the like. For instance, the proximal hub 52 can include a Luer lock fitting, a threaded fitting, a snap-lock fitting, or the like. In addition, the locking member 70 preferably incorporates a seal between the proximal hub 52 and the elongate member 60 so that blood or other fluid does not flow retrograde out the proximal end 22 of the catheter 20. For example, the locking member 70 can include a hemostasis valve, e.g. pinhole or duckbill valve, or a combination thereof, or a Tuohy-Borst type cap.

The elongate member 60 can be a tube or a rod with the central lumen 62 extending over the length thereof. For example, the elongate member 60 can be formed from a catheter or hypotube. The elongate member 60 should be of sufficient flexibility in order to be inserted into the lumen 26 of the catheter 20. On the other hand, the elongate member 60 should be provided with sufficient stiffness to stretch the catheter 20, in particular, the self-expandable areas 32, 34 when fully inserted into the catheter 20. Thus, the elongate member 60 should have a longitudinal stiffness greater than that of the self-expandable areas 32, 34. The stretching process is performed by advancing the elongate member 60 into to the distal end 24 of the lumen 26 of the catheter 20. Once the elongate member 60 has reached this position and abuts either directly or indirectly the distal end 24 of the catheter 20, the catheter 20 can be stretched by applying an additional pushing force in the longitudinal direction of the elongate member 60. The elongate member 60 can then be temporarily affixed at the proximal hub 52 of catheter 20 using the locking member 70 in order to generate a sufficient and constant stretching force to maintain the collapsed configuration.

By retracting the elongate member 60 from the distal end 24 of the catheter 20, the pressure in the longitudinal direction of the catheter 20 is removed and the proximal and distal self-expandable areas 32, 34 can then expand into their "natural," expanded state. By removing the stretching force, the self-expandable areas 32, 34 then transition into their energetically favorable, expanded state, which is utilized for vessel occlusion. The elongate member 60 is removed completely from the catheter 20. As can be seen from FIG. 10, the distal self-expandable area 34 is completely covered with the cover 38 and has the shape of a sphere or ball. The proximal self-expandable area 32, in contrast, is only covered with the cover 38 at its proximal half, leaving the distal half formed by the mesh 35 to permit fluid infiltration. The proximal self-expandable area 32 generally has a greater length than the distal self-expandable area 34 and in addition is generally in the shape of a cylinder.

Figure 4:
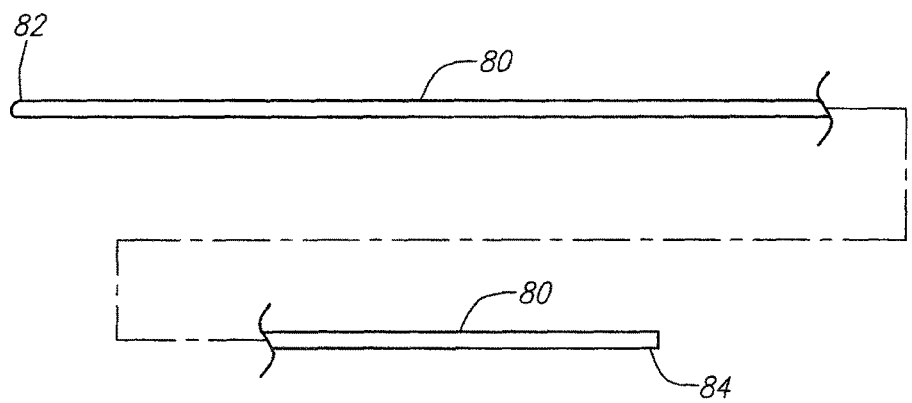
FIG. 4 illustrates a guidewire according to one embodiment.

FIG. 4 illustrates a guidewire 80 that is used in connection with the system 10. The guidewire 80 has a distal end 82 and a proximal end 84. The guidewire 80 is a conventional guidewire 80 that is dimensioned such that it can pass through the lumen 62 of the elongate member 60. The guidewire 80 is advantageously a "rapid exchange" type guidewire such that elongate member 60 and the catheter 20 can be advanced over the proximal end 84 of the guidewire 80 and advanced distally into position.

Figure 5:
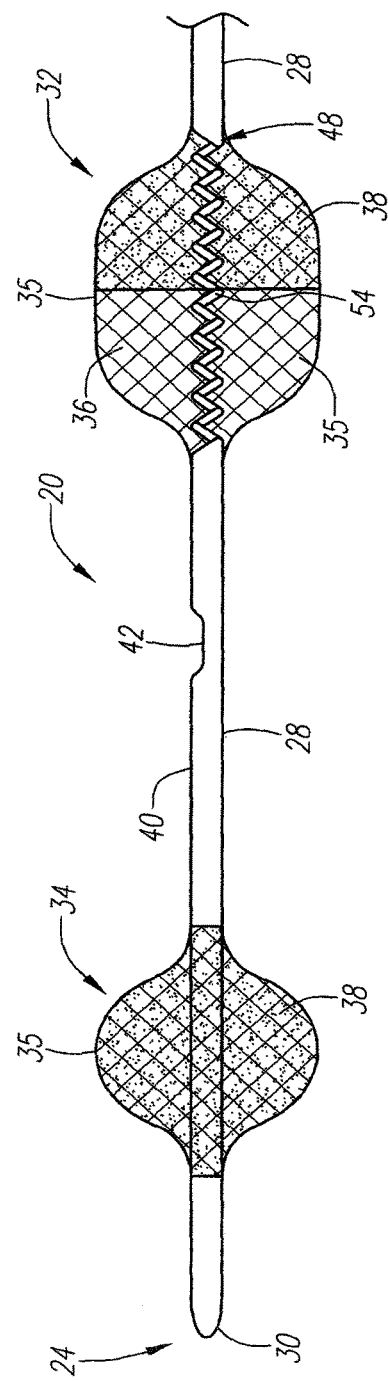
FIG. 5 illustrates a side view of a catheter according to another embodiment. The interior of a portion of the proximal self-expandable area is illustrated.

FIG. 5 illustrates an alternative embodiment of a catheter 20. In this embodiment, at least one of the self-expandable areas 32, 34 includes a spring 54 as the inner guide 48. The spring 54 is affixed at a proximal end to the catheter body portion 28 or shaft. The distal end of the spring 54 is affixed to the intermediate portion 40 of the catheter 20. The spring 54 applies a contraction force on the outer mesh 35, which causes the same to expand into the expanded or deployed state as illustrated in FIG. 5. While the outer component of the self-expandable area 32 is illustrated as a mesh 35 it should also be understood that the outer component can include a braid or net. In this embodiment, only a proximal portion of the mesh 35 is covered with the cover 38. The distal portion of the mesh 35 remains open via holes 36 to allow blood and other fluid to flow into the self-expandable area 32. In this embodiment, there is no need for holes to be provided in the catheter 20 to permit blood flow to enter the lumen 26. Rather, blood or other fluid in the interior of the self-expandable area 32 may just enter the lumen 26 directly.

The spring 54 thus provides the biasing or contraction force to move the self-expandable area 32 into the deployed state. The spring 54 also serves as the interior guide 48 for the elongate member 60. In this regard, the spring 54 is configured to permit passage of the elongate member 60 through the interior portion of the spring 54. The proximal and distal self-expandable areas 32, 34 can be collapsed by extending the elongate member 60 through the lumen 26 of the catheter 20 and extending or stretching the self-expandable areas 32, 34. The spring 54, given its flexible nature, expands when subject to this stretching force, thereby allowing the self-expandable area 32 to transition to the collapsed state. The spring 54 can by formed from a metallic or polymer-based material. For example, the spring 54 can be formed from NITINOL or a plastic or polymer such as polyester. While FIG. 5 illustrates the aperture 42 being located in the intermediate portion 40 of the catheter 20 it should be understood that the aperture 42 can be located within or straddle the self-expandable area 32.

Figure 6:
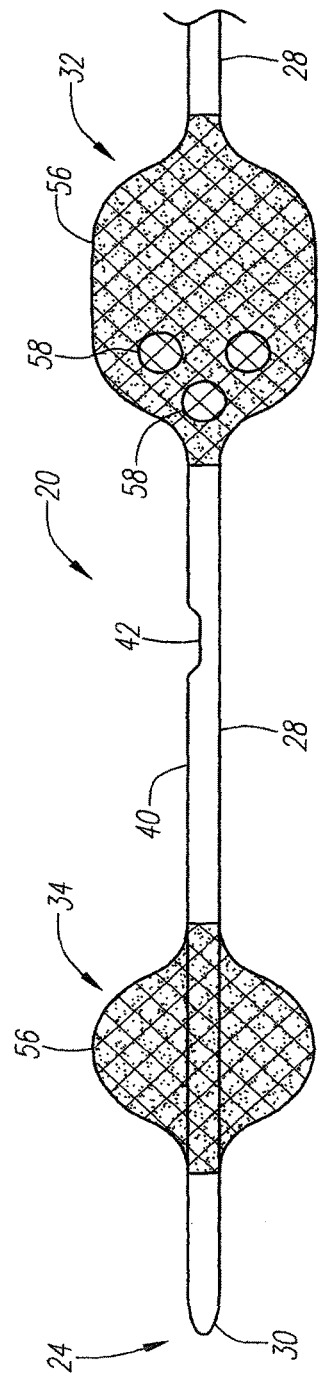
FIG. 6 illustrates a side view of a catheter according to another embodiment.

FIG. 6 illustrates yet another embodiment of a catheter 20. In this embodiment, the outer component of the self-expandable areas 32, 34, which can include a mesh 35, braid, or net is covered with a coating of elastic material 56. When the self-expandable areas 32, 34 are covered or otherwise coated with the elastic material 56, the self-expandable areas 32, 34 assume their deployed or expanded state as illustrated in FIG. 6. The elastic material 56 can include silicone, polyurethane, or PTFE. A biasing or stretching force must then be applied to the self-expandable areas 32, 34 to decrease their respective diameters to assume the collapsed state. The coating of elastic material 56 can be applied during manufacture of the self-expandable areas 32, 34. For example, the coating of elastic material 56 can be applied to the self-expandable areas 32, 34 when they are in the deployed or expanded state. The elastic material 56 will then retain this configuration by encapsulating or securing the underlying mesh 35 or other material forming the outer component.

The collapsed state can be achieved by insertion of the elongate member 60 into the lumen 26 of the catheter 20 and advancing the same until the distal end 24 is reached to apply a stretching force to move the self-expandable areas 32, 34 axially distally, thus resulting in diametric or radial collapse of the self-expandable areas 32, 24. The elongate member 60 utilizes a construction having high column strength. The coating of elastic material 56 can be separately manufactured and adhered or otherwise affixed to the mesh 35 or underlying support structure. Alternatively, the coating of elastic material 56 can be created by dipping, spraying, or other known applications.

As seen in FIG. 6, the coating of elastic material 56 covers all of the distally located self-expandable area 34. In contrast, a portion of the proximally located self-expandable area 34 is devoid of the coating of elastic material 56. For example, one or more holes or apertures 58 can be provided in the coating of elastic material 56 to permit blood and other fluid to enter the interior portion of the self-expandable area 32. Once inside, the blood or other fluid may enter the main lumen 26 as described herein with respect to the other embodiments. This may include holes located within an interior guide 48 or elsewhere on the catheter 20. Alternatively, the blood or other fluid may enter directly into the lumen 26 of the catheter 20.

Figure 7A:
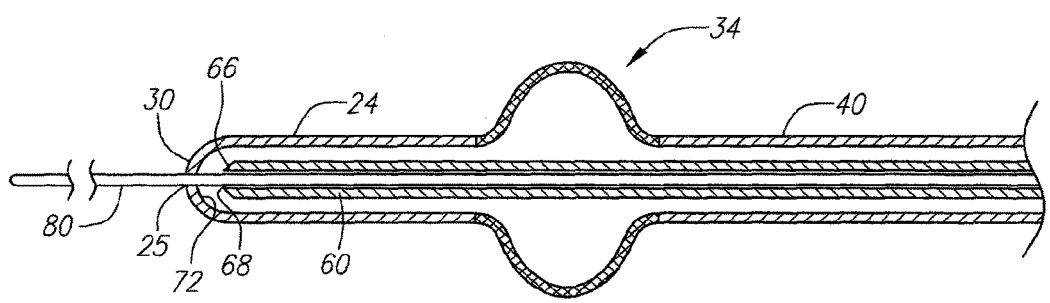
FIG. 7A illustrates a cross-sectional view of the distal end of a catheter according to one embodiment. The elongate member and guidewire are illustrated therein.

Referring now to FIG. 7, a cross-sectional view of the distal end 24 of a catheter 20 is illustrated according to one embodiment of the invention. As seen in FIG. 7, the distal end 24 of the catheter 20 includes a hole 25 dimensioned to permit passage of the guidewire 80 but not the elongate member 60. In this regard, a receiving surface 72 is formed on the interior portion of the catheter 20 that is configured to abut with the distal end 66 of the elongate member 60. During use, the elongate member 60 is advanced down the lumen 26 of the catheter 20 until the distal end 66 of the elongate member 60 contacts the receiving surface 72. Once contact is made, additional advancement of the elongate member 60 causes at least partial stretching of the self-expandable areas 32, 34 such that the self-expandable areas 32, 24 so that these are collapsed in a state like that illustrated in FIG. 2A. In FIG. 7A, the distal end 66 of the elongate member 60 is disposed away from the receiving surface 72 and, hence, the distally located self-expandable area 34 is shown in the expanded or deployed configuration.

Figure 7B:
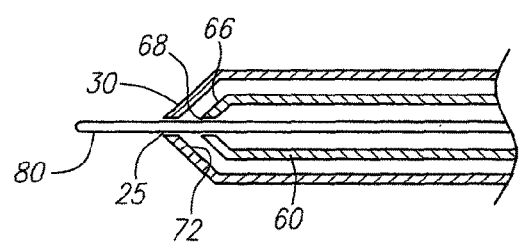
FIG. 7B illustrates a cross-sectional view of the distal tip of a catheter according to another embodiment. The elongate member and guidewire are illustrated therein.

It should be understood that the receiving surface 72 does not have to be located at the distal most end of the catheter 20 as illustrated in FIG. 7A. For example, the interior portion of the catheter 20 that is located distal to the self-expandable area 34 can be partially or completely solid (except for the hole 25 for the guidewire 80) to form a receiving surface 72 that is located at or distal to the self-expandable area 34. FIG. 7B illustrates another embodiment of a catheter 20 in which the receiving 72 surface is shaped in the form of a taper or the like. The distal end 66 of the elongate member 60 also is shaped to include a corresponding tapered surface to form a mating configuration when the elongate member 60 contacts or abuts the receiving surface 72 (the tapering angles of both the receiving surface 72 and the distal end 66 are substantially the same). While a taper or angled surface is illustrated, other configurations can also be employed.

FIG. 8 illustrates yet another embodiment of a catheter 20. In this embodiment, the catheter 20 incorporates a receiving member 74 located at least partially at the distal end 24 of the catheter. The receiving member 74 extends proximally within the catheter 20 and terminates at a receiving surface 72 that is configured to receive the distal end 66 of the elongate member 60. The receiving member 74 includes a lumen 76 therein that communicates with the hole 25 located at the distal tip of the catheter 20. The lumen 76 is sized to permit passage of the guidewire 80 but not permit passage of the elongate member 60. The receiving surface 72 can be tapered (e.g., configured as a cone) or otherwise configured to engage with the distal end 66 of the elongate member 60. In one aspect, the receiving member 74 extends proximally to at least the distal end of the self-expandable area 34. Of course, the actual point of termination of the receiving surface 72 may vary. For example, the receiving member 74 can terminate at a proximal end or region of the distally located self-expandable area 34.

The receiving member 74 can include a rod, tube, or channel that is bonded or otherwise affixed within the catheter 20. The receiving member 74 can be secured at the distal end to the distal end 24 of the catheter. Alternatively, or additionally, the receiving member 74 can be secured at its outer diameter or outer surface to the inner surface of the inner lumen 26 of the catheter 20. FIG. 8 illustrates the distally located self-expandable area 34 in the expanded state because the elongate member 60 is located proximal with respect to the receiving member 74. In order to collapse the self-expandable area 34, the elongate member 60 is advanced in the distal direction until the distal end 66 engages with the receiving surface 72 of the receiving member 74. After contact, additional distal displacement of the elongate member 60 at least partially stretches the self-expandable areas 32, 34 into their collapsed state. Conversely, when the elongate member 60 is retracted proximally from the catheter 20, the self-expandable areas 32, 34 transition back to their expanded state.

Figure 15A:
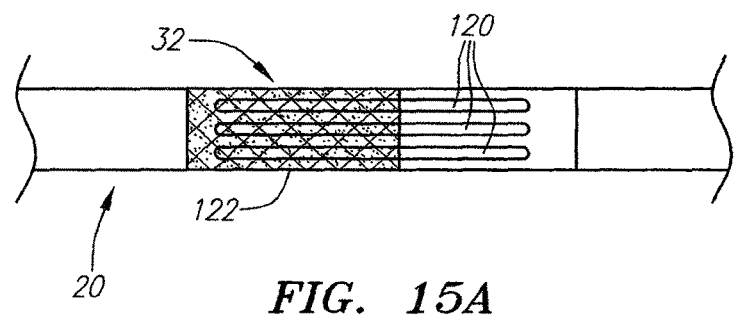
FIG. 15A illustrates a proximal self-expandable area according to one embodiment of the invention. The self-expandable area is illustrated in the collapsed state.
Figure 15B:
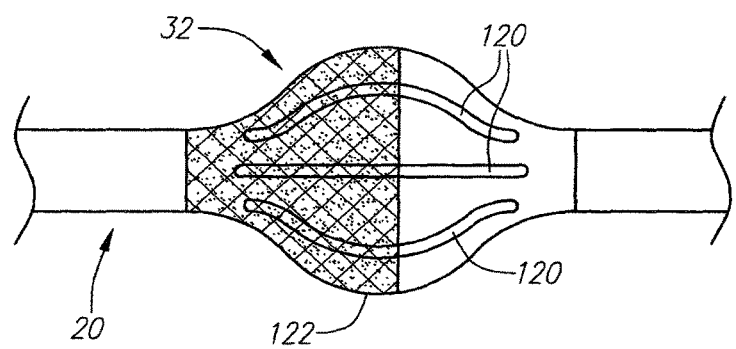
FIG. 15B illustrates the proximal self-expandable area of FIG. 15B. The self-expandable area is illustrated in the expanded state.

FIGS. 15A and 15B illustrate a catheter 20 according to another embodiment of the invention. In this embodiment, the construction of the catheter 20 is made into the self-expandable area 32, 34. FIG. 15A illustrates a proximally located self-expandable area 32 that includes a plurality of slots 120 formed in the wall of the catheter 20. The slots 120 allow the buckling of the catheter 20 into the deployed state of FIG. 15B. The self-expandable area 32 is in the collapsed state because of the insertion of the elongate member 60 (not shown). A portion of the slots 120 are covered via a cover 122 that forms a barrier for fluids. In this regard, the cover 122 forms the seal between the interior surface of the vessel and the catheter 20 when the self-expandable area 32 is in the expanded state as shown in FIG. 15A. The cover 122 may be formed from an elastic material that optionally aids in expanding the self-expandable area 32. The slots 120 may be dimensioned to permit passage of a working instrument 110. Similarly, the slots 120 permit body fluids such as blood to communicate with an interior lumen (not shown) of the catheter 20 so that the blood and other fluid may withdrawn via the catheter 20 as explained herein.

After retraction of the elongate member 60, the self-expandable area 32 expands outward in the radial direction as illustrated in FIG. 15B. This portion of the catheter body may be constructed from a segment that is biased to expand into this configuration in the absence of the stretching force. Of course, the elastic material of the cover 122 may also assist in the transition of the self-expandable area 32 to the state illustrated in FIG. 15B.

Figure 9:
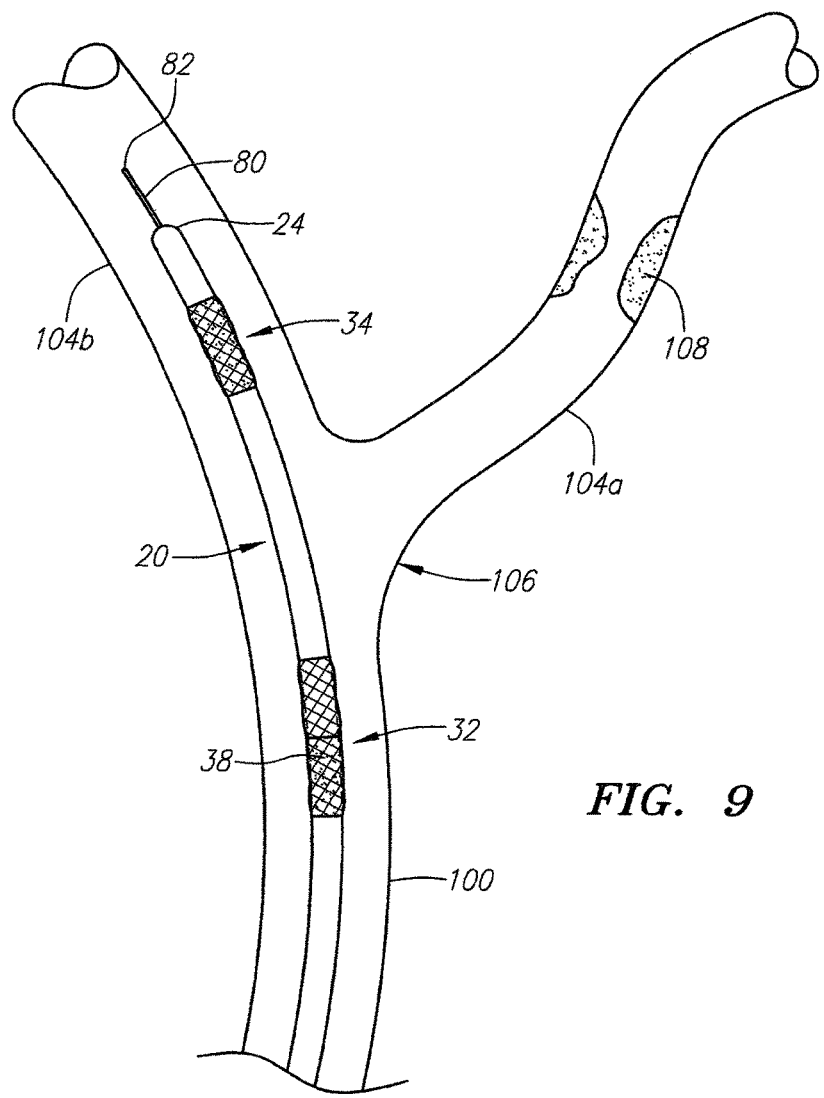
FIG. 9 illustrates the catheter being positioned within branch vessel of a bifurcation. The illustrated branch vessel that contains the catheter is the external carotid artery.

FIGS. 9-13 and 14A-14F illustrate use of the system 10 according to one aspect of the invention. FIG. 9 illustrates a bifurcated vessel 100 that includes a common vessel 102 and a plurality of branch vessels 104a, 104b. The branch vessels 104a, 104b branch from the common vessel 102 at a bifurcation 106. In one aspect of the invention, the vessels 102, 104a, 104b include cerebral vessels. For example, the common vessel 102 may include the common carotid artery while branch vessel 104a is the internal carotid artery and branch vessel 104b is the external carotid artery. As seen in FIGS. 9-12, a stenosis 108 or narrowing of the internal carotid artery 104a is shown that is treated with the system 10.

Figure 14A:
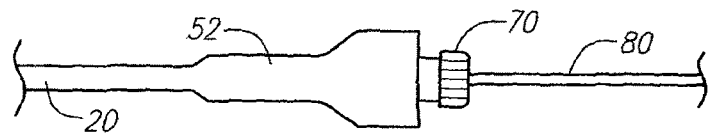
FIG. 14A illustrates the proximal end of the catheter along with the elongate member being locked or fixed with respect to the catheter. The guidewire is shown exiting the proximal hub of the catheter.

Initially, a guidewire 80 is introduced to the subject, typically through the femoral artery and is advanced until a distal end 82 reaches the external carotid artery 104b. Once the guidewire 80 is advanced in place, the catheter 20 is then inserted into the body over the guidewire 80. In this regard, the catheter 20 is advanced over the proximal end 84 of the guidewire 80 and is advanced distally. The catheter 20 is advanced and positioned in the collapsed state as illustrated in FIG. 9. Specifically, both the proximal and distal self-expandable areas 32, 34 are collapsed down as illustrated due to the stretching of the catheter 20 via the elongate member 60 that is disposed inside the lumen 26 of the catheter 20. FIG. 14A illustrates the elongate member 60 being inserted in the proximal end of the catheter 20. FIG. 14A also illustrates the locking member 70 that is secured to the proximal hub 52 of the catheter 20. The locking member 70 ensures that the proximal and distal self-expandable areas 32, 34 remain in the collapsed state.

Figure 14B:
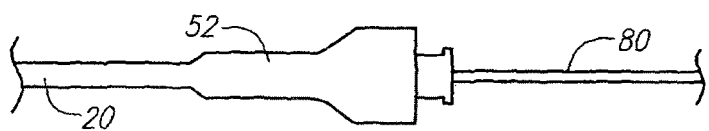
FIG. 14B illustrates the proximal end of the catheter after removal of the elongate member. The guidewire is shown exiting the proximal hub of the catheter.

The catheter 20 is then advanced beyond the common carotid artery 102 and the distal end 24 is introduced into the external carotid artery 104b. Once the distal end 24 is advanced a sufficient distance distal relative to the bifurcation 106, the elongate member 60 is withdrawn proximally relative to the catheter 20. This may include, for example, unscrewing the locking member 70 from the proximal hub 52 and withdrawing the elongate member 60 in the proximal direction. FIG. 14B illustrates the removal of the elongate member 60 from the catheter 20. As the elongate member 60 is withdrawn, the proximal and distal self-expandable areas 32, 24 expand substantially simultaneously as illustrated in FIG. 10.

Figure 10:
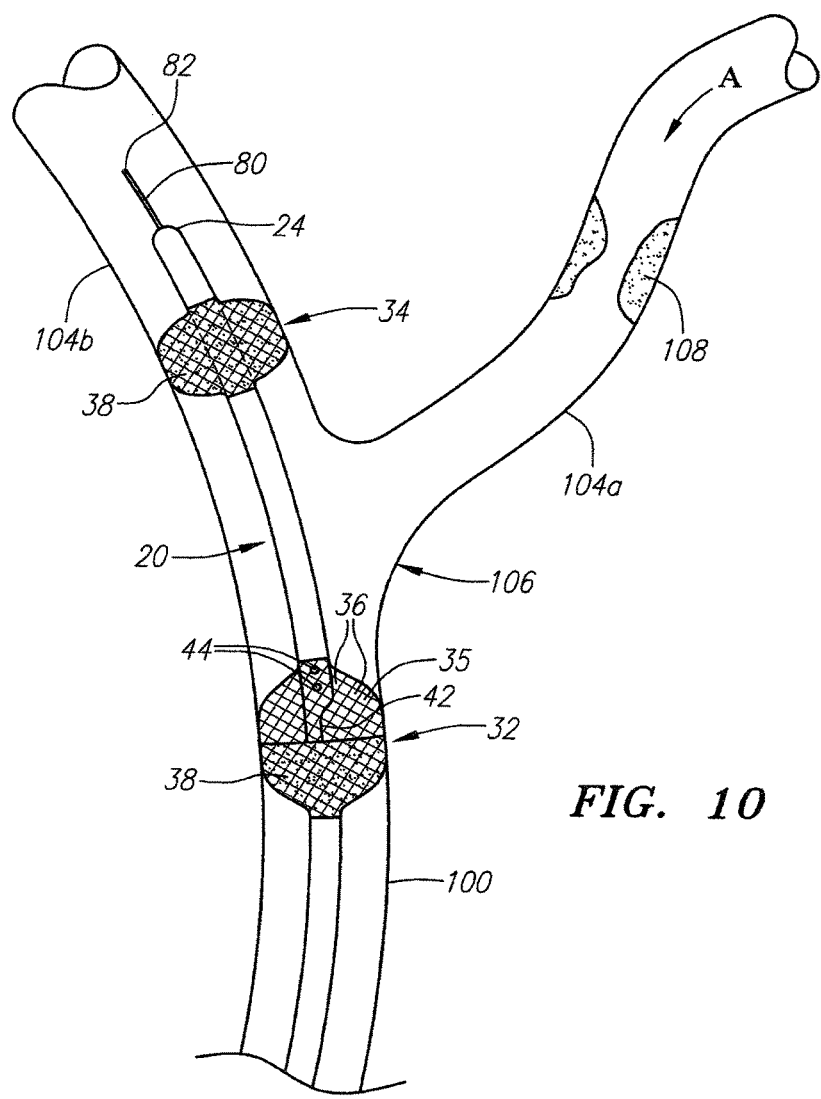
FIG. 10 illustrates the catheter of FIG. 9 wherein the proximal and distal self-expandable areas are expanded or deployed to occlude blood flow in the external carotid artery and the common carotid artery.

As seen in FIG. 10, because the distal self-expandable area 34 is covered at least on its distal side (FIG. 10 illustrates the distal self-expandable area being fully covered), the blood stream which is present within the common carotid artery 102 can no longer flow towards the external carotid artery 104b. At the same, the proximal self-expandable area 32 is deployed in the expanded state. Because of the additional occlusion of the common carotid artery 102, the blood flow in the internal carotid artery 104a is reversed from antegrade flow to retrograde flow in the direction of arrow A and is thus directed toward the common carotid artery 102. This "reversed" blood flow then enters the interior of the proximal self-expandable area 32 via the openings 36 in the mesh 35 and then passes into the inner lumen 26 of the catheter 20 via the holes 44. The cover 38 on the proximal self-expandable area 32 forms a sealing configuration with the internal walls of the vessel 102. The occlusion of the respective vessels 102, 104b can be tested by flushing radiographic contrast media into the vessels 102, 104b and observing the image using fluoroscopy or X-ray visualization equipment. Magnetic resonance angiography (MRA) can also be used to evaluate blood vessel patency.

Still referring to FIG. 10, after passing the mesh 35 (or net or braid), the blood or other fluid enters into the lumen 26 of the catheter 20 via the holes 44 of the catheter body 28. The proximal portion of the self-expandable area 32 that includes the cover 38 serves as a funnel for guiding or directing the blood stream into the lumen 26 of the catheter 20. Due to the reversal of blood flow direction from normal antegrade flow to reverse retrograde flow, the treatment of a stenosis 108 located within the internal carotid artery 104a can now be performed without hesitation.

Figure 11:
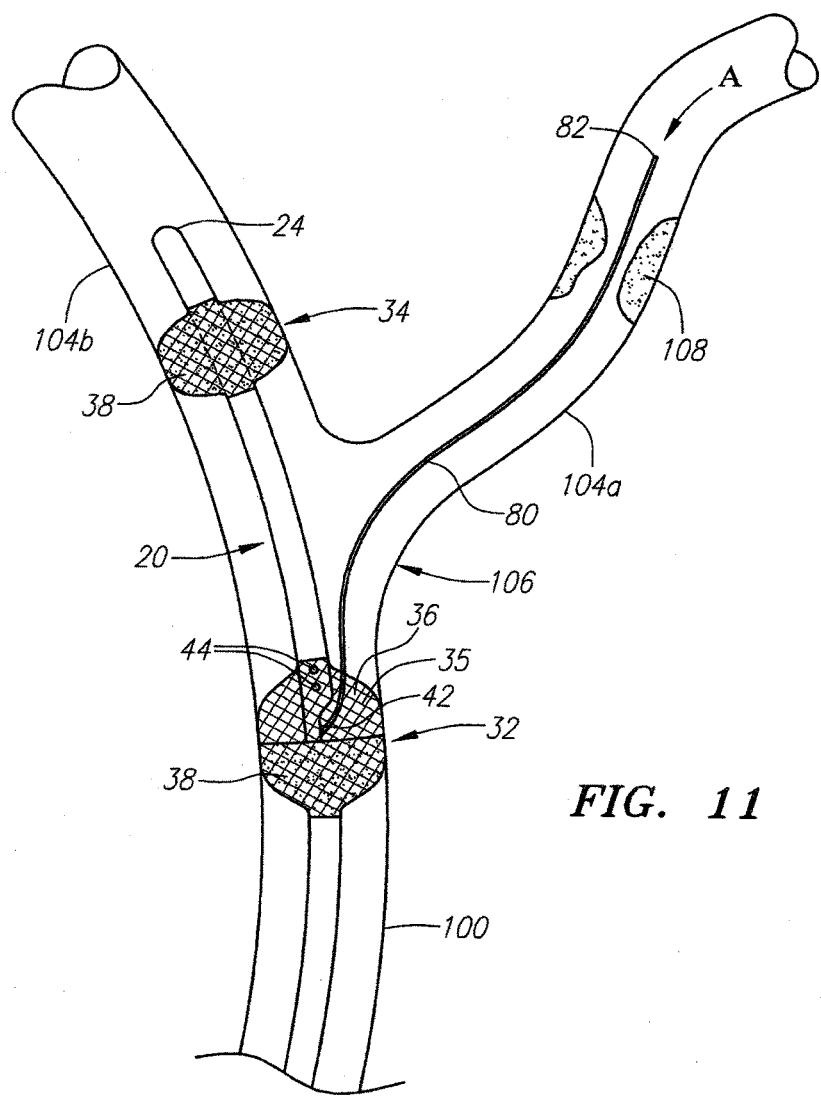
FIG. 11 illustrates the catheter of FIG. 10 wherein the guidewire has been first retracted proximally and then advanced distally into the internal carotid artery that contains a stenosis.
Figure 14C:
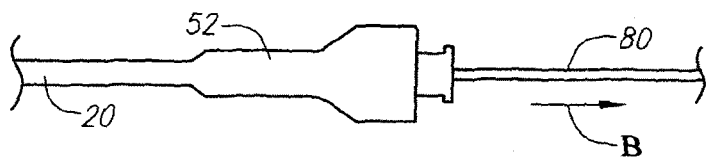
FIG. 14C illustrates proximal retraction of the guidewire relative to the catheter.
Figure 14D:
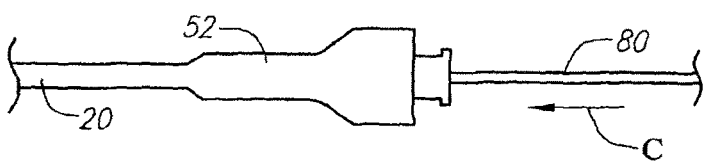
FIG. 14D illustrates distal advancement of the guidewire relative to the catheter.

With reference to FIG. 11, the treatment procedure continues with the guidewire 80 being retracted proximally within the catheter 20 until the distal end 82 of the guidewire 80 reaches the location of an aperture 42, which is provided at the side of the catheter 20. FIG. 14B illustrates proximal movement of the guidewire 80 in the direction of arrow B. While FIG. 11 illustrates the aperture 42 located within the proximal self-expandable area 32 it should be noted that the aperture 42 can be located within the intermediate portion 40 of the catheter 20 or even straddle the proximal self-expandable area 32. At this position the guidewire 80 is then advanced distally to pass through the aperture 42 and out of the self-expandable area 32. FIG. 14C illustrates distal movement of the guidewire 80 relative to the catheter 20 in the direction of arrow C. In this regard, the guidewire 80 can pass through one of the openings 36 formed in the mesh 35 of the self-expandable area 32. As seen in FIG. 11, the guidewire 80 is further advanced to enter into the internal carotid artery 104a and reach and/or cross the stenosis 108.

Figure 14E:
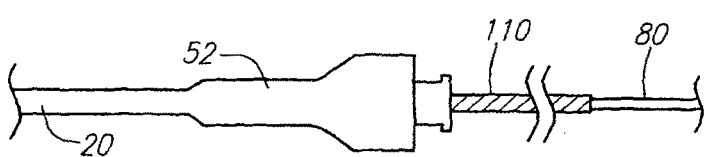
FIG. 14E illustrates the proximal end of the catheter along with an interventional tool being advanced over the guidewire.

With reference to FIGS. 12 and 14E, one or more intervention tools 110 can now be inserted via the lumen 26 of the catheter 20 over the guidewire 80. The interventional tool 110 can include a balloon catheter or stent catheter having an expandable member 112 thereon. The expandable member 112 can inflate to open or widen the stenosis 108. Alternatively, an interventional device such as a stent, atherectomy device, or the like (not shown) can be deployed within the stenosis 108 by the interventional tool 110. In one aspect of the invention, an interior guide 48 is provided within the proximal self-expandable area 32. The interior guide 48 enables the intervention tool 110 to be brought to the desired location without hitting the transition of the self-expandable area 32 to the intermediate region 40.

Because the retrograde or reverse direction of blood flow generated by the deployed self-expandable areas 32, 34 any particulate matter, such as thrombosis, atheroma, or the like, which may detach or slough off from the stenosis 108 during the treatment will be transported in the direction of arrow A toward the proximal self-expandable area 32 from where they can be removed via the lumen 26 of the catheter 20. The blood or other fluid that may contain particulate matter can then be filtered or treated and reintroduced to the patient. For example, the blood can be subject to filtration and then introduced into the patient's venous system.

Figure 13:
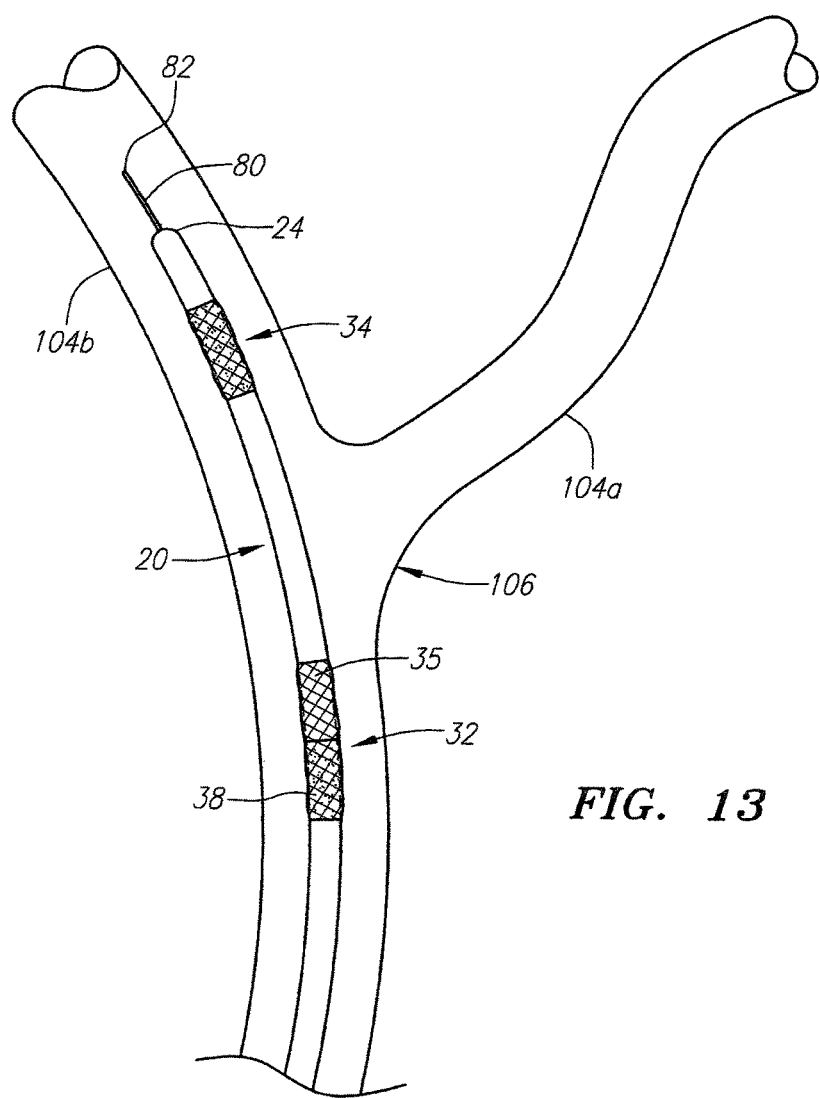
FIG. 13 illustrates the catheter of FIG. 12 with the working instrument withdrawn. In addition.
Figure 14F:
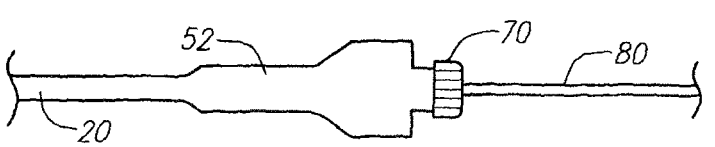
FIG. 14F illustrates the proximal end of the catheter along with the elongate member after the elongate member has been re-introduced over the guidewire and into the lumen of the catheter to collapse the proximal and distal self-expandable areas.

FIGS. 13 and 14F illustrate the system 10 after the interventional tool 110 has been retracted proximally from the catheter 20. In addition, FIGS. 13 and 14F illustrate the re-introduction of the elongate member 60 over the guidewire 80. The elongate member 60 is advanced over the guidewire 80 until the distal end 82 of the guidewire 80 contacts the receiving surface 72 of the catheter 20. Additional distal advancement of the elongate member 60 then stretches the proximal and distal self-expandable areas 32, 34 into their collapsed state as seen in FIG. 13. In addition, the elongate member 60 can be secured to the proximal hub 52 of the catheter 20 via the locking member 70. The catheter 20 and guidewire 80 can then be withdrawn proximally and ultimately removed from the subject. As shown in FIG. 13, the former stenosis 108 is now gone (or reduced) after treatment with the interventional tool 110.

While the method described above has been mainly described with regards to the treatment of carotid vessels it should be understood that the invention can be applied to other vessels, in particular, the treatment of one or more branches of a bifurcated vessel. Because the invention permits access to a blocked region between two expanded areas, it can also be applied to other tubular vessels where the treatment site is located between the two expanded areas.

The above-described system 10 is easier to use than prior systems because a single device employs both proximal and distally located occlusive elements that can be simultaneously deployed simply by retraction of the elongate member 60. The system 10 avoids the need for separate inflation lumens and can thus be made with a relatively small cross sectional area (e.g. 7 F or less). The system 10 is also advantageous because a single guidewire 80 can be used to both positioning of the catheter 20 as well as the interventional tool(s) 110. Normal or antegrade flow in the patient can be quickly re-established in the patient simply by insertion of the elongate member 60 over the pre-placed guidewire 80. Finally, conventional imaging techniques can be used to view the entire interventional procedure using the system 10 described herein.

Figure 16:
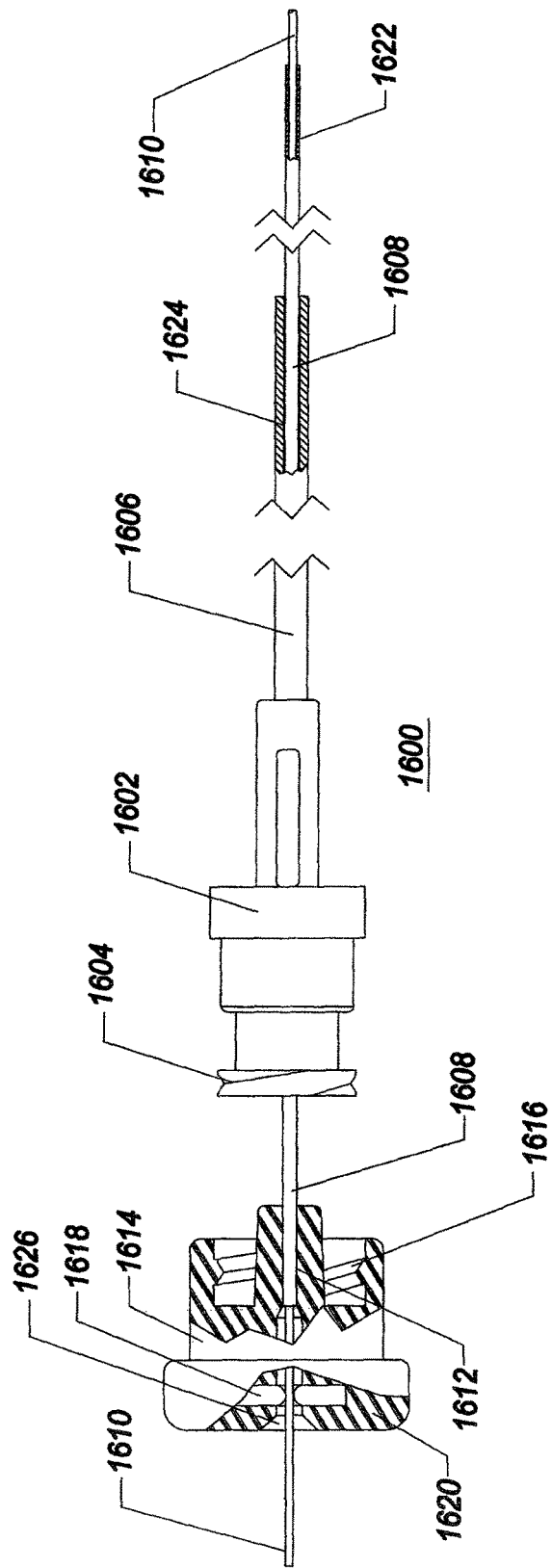
FIG. 16 illustrates a two-stage pusher configured to separately engage and activate a proximal expandable region and a distal expandable region of a flow reversal embolic protection catheter.

FIG. 16 illustrates the proximal end of a two-step stylet or two-stage pusher 1600, shown in partial breakaway view, suitable for use with the flow reversal system 10 described herein. The two-step stylet or two-stage pusher 1600 comprises a first hub 1602 further comprising a first hub locking adapter 1604, a second hub 1614 further comprising a second hub locking adapter 1616, a second hub hemostasis valve 1620 further comprising a seal insert 1618 and a tapered entry path 1626, an inner pusher tube 1608, an inner tube to second hub bond joint 1612, an outer pusher tube 1606, an outer pusher tube to first hub bond joint (not shown), and a guidewire 1610.

Figure 20:
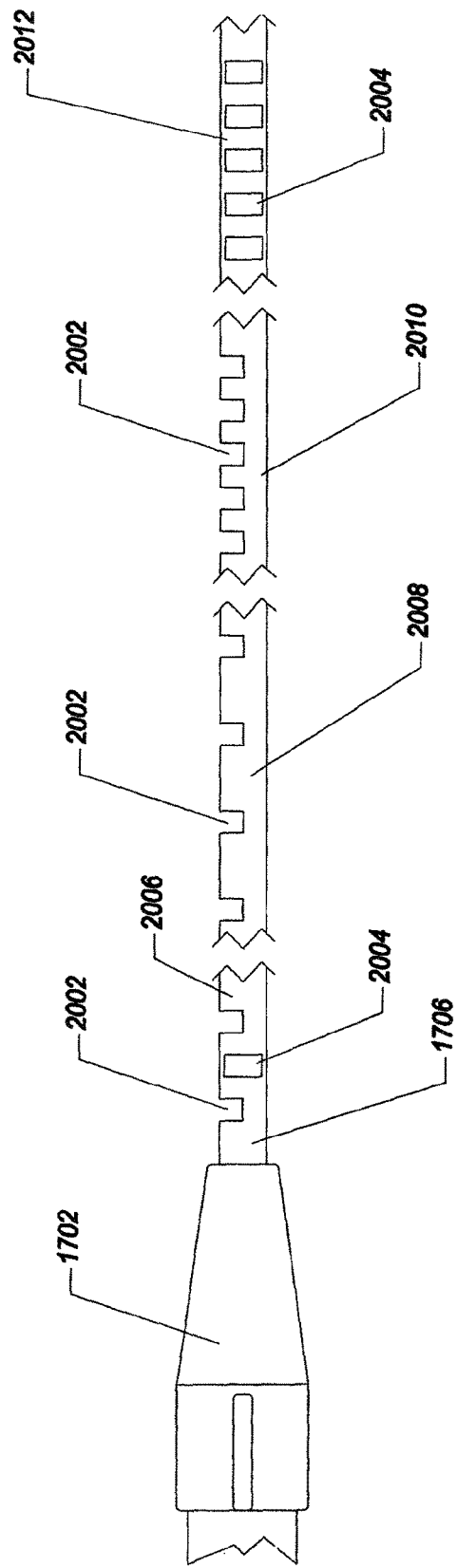
FIG. 20 illustrates the hub and several regions of the catheter shaft where the shaft regions comprise cutouts in various configurations to enhance and control shaft flexibility.

Referring to FIG. 16, the inner pusher tube 1608 comprises a hollow central lumen 1622 through which the guidewire 1610 slidably moves while being radially constrained within certain tolerance limits. The outer pusher tube 1606 comprises a hollow central lumen 1624 through which the inner pusher tube 1608 slidably moves and is radially constrained. The outer pusher tube 1606 can be a solid tube, or it can have slits or slots cut into the tubing wall to form a "snake-cut" pattern to enhance flexibility. The inner pusher tube 1608 can likewise be solid or have slot patterns cut into the tubing wall to generate regions of controlled flexibility. In a preferred embodiment, the inner pusher tube 1608, the outer pusher tube 1606, or both, can comprise regions of increasing flexibility moving from the proximal end to the distal end of the pusher 1600. Flexibility in two directions can be achieved by generating the slits into the tubing wall from orthogonal directions, generally with offset longitudinal locations along the axis of the tubing in order to generate the "snake-cut". The slits can have widths ranging between 0.005 and 0.050 inches and they can be configured to transect the tube across approximately ½ of its diameter, or slightly less. A pair of slits can be generated at the same axial location as long as some material, approximately 0.005 inches or more remains between the slits. The regions of increased flexibility can be achieved by placing the slits or slots more densely along the length of the tubing. FIG. 20 illustrates tubing slits 2002, 2004 as applied to the catheter shaft 1706 but the same types of cuts 2002, 2004 would be suitable for the pusher 1600.

The outer pusher tube 1606 can be bonded, welded, insert molded, pinned, or otherwise affixed to the first hub 1602 such that axial movement of the first second hub 1614 relative to the first hub 1602 results in the inner pusher 1608 to move axially relative to the outer pusher tube 1606. The first hub locking adapter 1604 is integral, or affixed, to the first hub 1602 and a central lumen (not shown) of the first hub 1602 is operatively connected to the outer pusher central lumen 1624. The hemostasis valve 1620 is affixed, or integral, to the second hub 1614. The seal insert 1618 is trapped concentrically so that its central through lumen is aligned with the central lumen 1622 of the inner pusher tube 1608. The seal insert 1618 can be a pinhole membrane, a duckbill valve, a Tuohy-Borst valve, a combination thereof, or the like. The seal insert 1618 can be fabricated from elastomeric materials such as, but not limited to, thermoplastic elastomer, silicone elastomer, polyurethane, latex rubber, or the like. The hardness of the seal inert 1618 can range from 5 A to 90 A, with a preferred range of 30 A to 72 A. The seal inset 1618 can be coated or impregnated with lubricity enhancing materials such as, but not limited to, hydrophilic polymers of polyurethane base, silicone oil, or the like. The first hub 1602 and the second hub 1614 can be fabricated from relatively rigid polymers such as, but not limited to, polycarbonate, polyester, polyimide, polyimide, polyvinyl chloride, acrylonitrile butadiene styrene, or the like.

The guidewire 1610 can be a typical guidewire ranging in diameter from 0.008 to 0.025 inches, with a preferred diameter range of 0.010 to 0.017 inches. A commonly used guidewire has a diameter of about 0.014 inches. The length of the guidewire can range between 45-cm and 200-cm with a preferred length range of 100 to 150-cm. The guidewire can be bare metal or it can be coated, for example with PTFE, a hydrophilic coating, or other slip layer. The guidewire can have straight tip, a J-tip, or other configuration suitable for navigating the vasculature.

Figure 17:
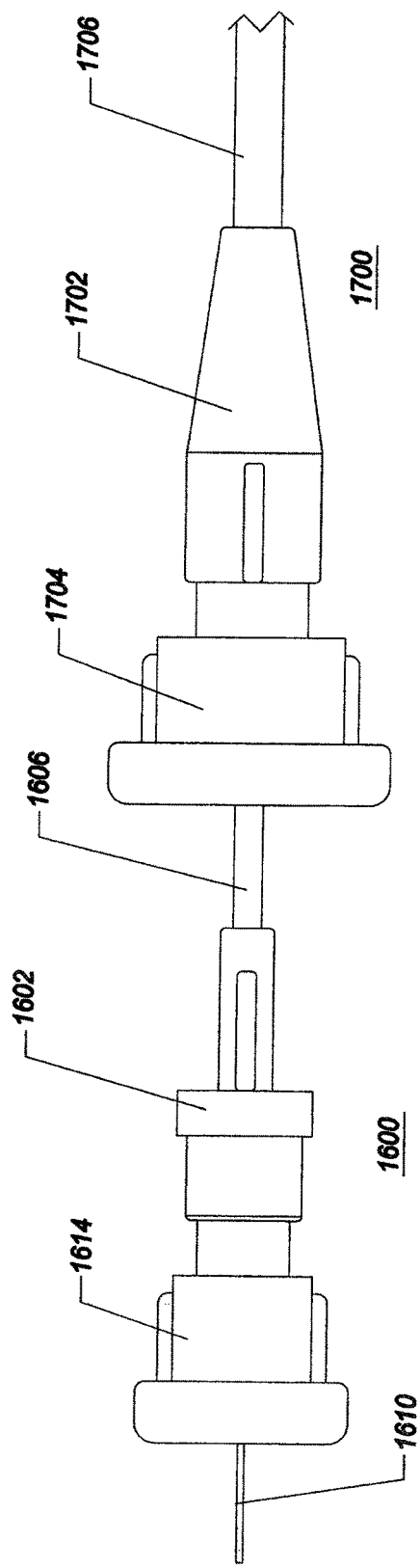
FIG. 17 illustrates a proximal end of the two-stage pusher shown in relationship with the proximal end of the flow reversal embolic protection catheter.

FIG. 17 illustrates the two-part pusher 1600 shown in working relationship with the proximal end of a flow reversing embolic protection catheter 1700. The two-part pusher 1600 comprises the illustrated first hub 1602, the second hub 1614, the outer pusher tube 1606, and the central guidewire 1610. The proximal end of the flow reversing embolic protection catheter 1700 comprises the catheter hub 1702, a catheter hemostasis valve 1704, and the proximal region of the outer catheter shaft 1706.

Referring to FIG. 17, the outer pusher tube 1606 slides axially within the catheter hub 1702, within a central lumen of the hemostasis valve 1704, and a lumen of the outer catheter shaft 1706. The hemostasis valve 1704 is similar in construction to the catheter hemostasis valve 1620 of FIG. 16, but comprises a somewhat larger diameter sealing capability to accommodate the outside diameter of the outer pusher tube 1606. In an embodiment, the catheter hemostasis valve 1704 can comprise a Tuohy-Borst type tightening or constricting valve that can be used to selectively lock the outer pusher tube 1606 in place, using friction, interference, or part engagement, relative to the catheter hub 1702.

FIG. 18A illustrates a side view, in partial breakaway, of the flow reversing embolic protection catheter 1700, taken in a central region near but not at the distal end of the catheter 1700. The catheter 1700 comprises the proximal expandable mesh 1820, a proximal mesh distal bond 1806, the outer pusher tube 1606, the inner pusher tube 1608, a proximal bumper 1818, a tapered region 1814, a proximal plug 1812 that forms a stop for the outer pusher tube 1606, a funnel 1818 at the proximal end of the plug 1812 that tapers to a central plug lumen 1816, a distal expandable mesh proximal bond 1824, a distal expandable mesh 1822, a catheter proximal length change region 1836, and a catheter distal length change region 1834.

Referring to FIG. 18A, the outer pusher tube 1606 can be advanced against the proximal plug 1812. The outer pusher tube 1606 can be forced against the funnel 1818 which coerces the distal end of the outer pusher tube 1606 to become generally centered within the catheter. The outer pusher tube 1606 is too large in diameter to pass through the central lumen 1816 and so the outer pusher tube can selectively be used to exert distal axially directed force against the plug 1812. This distal force on the plug 1812 can cause the proximal length change region 1836 to become longer forcing the proximal expandable mesh 1820 to collapse diametrically, radially, or in cross-sectional area. Proximal withdrawal of the outer pusher tube 1606 can remove the distal axial force on the plug 1812 allowing the proximal expandable mesh 1820 to seek its biased, larger diameter, shorter length configuration. The inner pusher tube 1608, optionally surrounding the guidewire 1610, as illustrated in FIG. 16 is centered by the outer pusher tube 1606 and can slidably extend through the central lumen 1816 of the proximal plug 1812 and on into the more distal regions of the catheter. The inner pusher tube 1608 can slide freely within the outer pusher tube 1606 thus allowing independent control of the expansion of the proximal expandable mesh 1820 and the distal expandable mesh 1822.

FIG. 18B illustrates a side view of the catheter 1700 with the distal bond 1826 region of the distal expandable mesh 1822 in expanded view. The distal bond 1826 region further comprises the distal length change region 1834, a guidewire 1610, the inner pusher tube 1608, a distal tip 1832 further comprising a distal coil 1842, and a distal plug 1830 further comprising a plug central lumen 1838, and a tapered funnel region 1840.

Referring to FIG. 18B, the inner pusher tube 1608 is advanced against the tapered funnel region 1840 of the distal plug 1830. The inner lumen of the inner pusher tube 1608 comprises the guidewire 1610 slidably disposed therein. The funnel region 1840 allows the guidewire 1610 to be advanced against the distal plug 1830 and to become coerced concentrically medial within the funnel region 1840 so that the guidewire 1610 can advance slidably through the central lumen 1838 of the plug 1830. The distal tip 1832, in the illustrated embodiment, is a length of polymeric tubing. The distal bond 1826 of the distal expandable mesh 1822 is affixed to the exterior of the distal tip 1832. The distal plug 1830 is affixed to the interior of the distal tip 1832. Thus, when the inner pusher tube 1608 is advanced distally thereagainst, the plug 1830 can be forcibly advanced distally by the inner pusher tube 1608. This forcible advancement of the distal end of the distal bond 1826 lengthens the length changeable region 1834 causing the distal expandable region 1822 to collapse radially or diametrically. When the inner pusher tube 1608 is withdrawn proximally, the axial force against the plug 1830 is removed and the distal expandable region 1822 can expand radially, in cross-sectional area, or diametrically to seek its pre-biased configuration to the extent permissible by the inner diameter of the blood vessel or other body conduit through which the catheter 1700 is advanced.

The distal coil 1842 comprises a central through lumen, not illustrated, suitable for slideable advancement of the guidewire 1610 therethrough. The distal coil 1842 can be fabricated from metal such as, but not limited to, stainless steel, titanium, Nitinol, tantalum, platinum, gold, iridium, cobalt nickel alloy, a combination thereof, or the like. The spacing between the coils can range from approximately 0 to approximately 10 times the coil wire diameter. The distal coil 1842 can be fabricated from wire with a round, oval, rectangular, or other suitable cross-sectional characteristic.

FIG. 19A illustrates a side view of a embolic protection catheter 1700 comprising the proximal catheter shaft 1706, the proximal expandable mesh 1820, the proximal bond 1804 of the proximal expandable mesh 1820, the distal bond 1806 of the proximal expandable mesh 1820, a plurality of aspiration holes or vent ports 1904, a sideport 1906, the proximal length change region 1836, a transition zone 1908, the distal expandable mesh 1822, the proximal bond 1824 of the distal expandable mesh 1822, the distal length change region 1834, the distal tip 1832, and the guidewire 1610.

Referring to FIG. 19A, the proximal catheter tubing 1706 can have an outer diameter ranging between 1 French and 18 French. The inner diameter of the proximal catheter tubing 1706 can range from 0.5 French in the smallest sizes to 17 French in the largest sizes. The vent holes 1904 can have diameters ranging from 0.005 inches to 0.125 inches. The aspiration holes or vent ports 1904 can be round, elliptical, rectangular, oval, or comprise any other suitable cross-sectional shape. The combined area of the aspiration or vent holes 1904 should be equal to, or greater than, the cross-sectional area of the inner lumen of the proximal catheter tubing 1706 to minimize flow restriction through the catheter 1700. The transition zone 1908 divides the proximal region of the catheter 1700, having a greater stiffness, from the distal region of the catheter 1700, having a lesser stiffness and greater flexibility. The transition zone 1908 can be all polymeric, can be all metal, or can be a reinforced structure comprising a tapered metal or polymeric coil sandwiched between or affixed inside a polymeric catheter tube. The transition zone 1908 is illustrated distal to the distal bond 1806 but can, in another embodiment, reside proximal to the distal bond 1806. In this alternative embodiment, the diameter of the distal bond 1806 is smaller than the diameter of the proximal bond 1804 in order to match the diameter between the bond and the tubing to which the bonds are affixed. The distal bond 1806 and the proximal bond 1804 can comprise glue or adhesive joints, they can be wound or wrapped with polymeric or metal strands, they can be embedded within layers of axially elongate cylindrical polymers, or the like.

The proximal length changing region 1836 and the distal length changing region 1834 can be fabricated in similar ways. The length changing regions 1836, 1834 can comprise braided or coil structures fabricated from polymers or metals. Polymers suitable for the length changing regions 1836, 1834 include, but are not limited to, polyester, Hytrel, PEEK, polyimide, polyamide, PEN, silicone elastomer, polyurethane, or the like. The braided or coil structures are preferably not restricted in diameter since diameter changes, especially in the braided structure, are beneficial during changes in length. Coiled structures can perform length change without substantial amounts of diameter change and are, therefore, preferred in for this type of application. Polymeric layers can be placed internal to the coil or braid as well as externally, but these polymeric layers should not be bonded or affixed to the coils or braids such that motion is restricted substantially.

In another embodiment, rather than using a two-step stylet or two stage pusher, multiple stylets can be used to separately adjust the proximal expandable mesh 1820 and the distal expandable mesh 1822. The plurality of separate stylets can be arrayed along the longitudinal axis of the catheter 1700. The multiple separate stylets can be arrayed within a single lumen (not shown) or each within their own separate lumens (not shown) in the catheter tubing 1706. Each stylet can have its own control knob or feature at the proximal end to permit selective motion of the separate stylets.

In yet another embodiment, the proximal length changing region 1836 or the distal length changing region 1834 can be magnetically activated to force the ends apart or to attract the ends together. Thus, the length changing regions 1834, 1836 can be made to move passive expandable meshes 1822 and 1820, respectively, rather than having the expandable meshes 1822 and 1820 be shape-memory structures. In another embodiment, the length changing regions 1834, 1836 can be activated by shape memory transition in response to exposure to blood at body temperature or in response to Ohmic or resistive heating generated by applying electrical current to the catheter 1700. In an embodiment, body temperature can be used to cause the mesh 1820, 1822 to expand diametrically. In this same embodiment, the application of resistive heating to the length changing regions 1836, 1834 to expand with greater force than that exerted by the meshes 1820, 1822, thus collapsing the meshes 1820, 1822 diametrically. Combinations of mechanical (stylets), shape memory effects, and magnetism can be used in controlling the expansile characteristics of the catheter 1700.

FIG. 20 illustrates an embodiment of the proximal catheter tubing 1706 of FIG. 17. In this embodiment, the proximal catheter tubing 1706 is affixed to a hub 1702. The tubing 1706 has four areas or regions of flexibility. These regions of flexibility, listed proximal to distal on the catheter shaft are 2006, 2008, 2010, and 2012. Regions 2006, 2008, and 2010 comprise a plurality of top-cuts 2002 which are configured to impart a controlled amount of flexibility to the proximal catheter tubing 1706 in the up and down directions. Furthermore, regions 2006 and 2012 comprise a plurality of side-cuts 2004 which impart flexibility into and out of the plane of the page. The number of top-cuts 2002 per unit length and the axial length of each top-cut 2002 can be adjusted to control flexibility. For example, more distal regions 2010 and 2012 of the proximal catheter tubing 1706 can have more side cuts 2002, 2004, or both, per unit length to promote increased flexibility relative to the more proximal regions 2008, which can have less or no side-cuts 2004. The most proximal region 2006 is illustrated with both top-cuts 2002 and side-cuts 2004. The top-cuts 2002 and the side cuts 2004 can be imparted into metal tubing using laser etching, photo etching, electron discharge machining, and the like. The cuts 2002, 2004 can be generated in polymeric tubing using laser cutting, traditional machining, die cutting, or the like. The cuts 2002, 2004 are also known as snake cuts since they allow snake-like flexibility. The catheter 1700 can comprise between one and 10 regions of different flexibility with a preferred range of two to six regions of different flexibility. This type of construction is especially beneficial in adding flexibility to the tubes 1606 and 1622 of the metal pusher 1600.

FIG. 21 illustrates a step-down or transition zone within a catheter shaft 2100. The catheter shaft 2100 comprises the proximal polymeric layer 2102, the transition polymeric layer 2106, the distal polymeric layer 2104, and the coil 2108. The coil 2108 forms a continuous winding across the step-down or transition zone, which is a benefit in reducing manufacturing costs and improving catheter strength. In the illustrated embodiment, the coil 2108 has spaces between the windings. The space between the windings can range from 0 to approximately 10 wire widths with a preferred range of 0 to 5 wire widths. In another embodiment, the coil 2108 can be configured with minimal or no spaces between the windings. In yet another embodiment, the coil 2108 has spaces between the windings on the larger side of the tapered transition zone and approximately no distance between the windings in the smaller diameter region following the step-down transition. The coil 2108 can be fabricated from flat wire, round wire, rectangular wire, wire with oval cross-section, and the like. The coil 2108 can be fabricated from tempered, full spring hardness stainless steel, malleable stainless steel, tantalum, cobalt nickel alloy, titanium, Nitinol, and the like. The coil 2108 can be coated with radiodense materials such as, but not limited to, tantalum, gold, platinum, platinum iridium, and the like to enhance radiopacity. The step-down or transition zone as illustrated is suitable for use in the region 1814 from FIG. 18A, for example. The step-down transition zone is also suitable for the region encompassing the plug 1830 in FIG. 18B. In this area, the wire winding can support or even replace the plug 1830 and the winding can extend continuously out beyond the end of the catheter tip to form the flexible fixed guide tip coil 1842.

FIG. 22A illustrates a length of axially elongate, composite tubing 2200 fabricated in layers and comprising an intermediate reinforcing coil 2202, an inner layer 2204 having a central lumen 2210, and an outer layer 2206.

Referring to FIG. 22A, the multi-layer catheter tubing 2200 is generally fabricated over a mandrel (not shown). The mandrel is generally axially elongate, round in cross-section and is fabricated from stainless steel with a PTFE outer coating to facilitate removal of the mandrel once the assembly 2200 is completed. The inner layer 2204 is first placed over the mandrel, preferably with a diametric clearance of about 0.001 to 0.005 inches. The reinforcing coil 2202 is next assembled over the inner layer either in one piece or wound around the inner layer 2204 pre-mounted over the mandrel. The coil 2202 can be wound using a coil winder, lathe and suitable wire delivery hardware, or the like. The coil 2202 is next fastened in place at the ends and the outer layer 2206 is slipped over the coil 2202 with sufficient clearance to permit coaxial movement. A length of heat shrink tubing (not shown), generally fabricated from PET or PTFE is next aligned over the outer layer 2206. Using a heat source that surrounds the heat shrink tubing, the heat shrink tubing is heated and reduced in diameter to melt the inner layer 2204 to the outer layer 2206 through the spacing between the windings of the coil 2202. The heat shrink tubing also generates radial inward force distributed sufficiently evenly to coerce the two layers 2204 and 2206 together. Once the heating or welding process is completed, the heat shrink tubing can be cut off or otherwise removed, and the mandrel can be removed leaving the inner lumen 2210 within the composite tubing 2200. The resulting thickness of the composite tubing wall can range between 0.005 and 0.025 inches with a preferable range of 0.005 and 0.015 and a most preferred range of 0.008 to 0.012 inches.

The inner layer 2204 and the outer layer 2206 can be fabricated from polymeric materials such as, but not limited to, polyurethane, polyethylene, polypropylene, polyester, Hytrel, silicone elastomer, thermoplastic elastomer, PEEK, polyvinyl chloride, and the like. The inner layer 2204 and the outer layer 2206 need not be the same material but they should be able to bond or weld together with the applied heat of the fabrication process; thus they should have approximately similar glass-transition or melt temperatures. Materials and configurations suitable for use in fabricating the coil 2202 are described elsewhere in the specification for the coil 2108 of FIG. 21. This composite structure 2200 has the benefit of good column strength, good torqueability, excellent kink resistance, and thin wall, all useful features for catheter construction. The tensile strength of the coil reinforced composite structure 2200 is not as high as other configurations. This type of tubing construction is suitable for the inner member or the outer member 1706. In the case of the outer member 1706, the inner diameter of the completed tubing can range between 4 and 8 French with a preferred range of 5 to 7 French, where French indicates the diameter of the tubing in mm times a factor of 3. Thus, a 2 mm diameter tube has a 6 French diameter.

FIG. 22B illustrates a length of axially elongate tubing 2220 fabricated in layers and comprising an intermediate reinforcing braid 2222, an outer layer 2206, and an inner layer 2204 further comprising a central lumen 2210.

Referring to FIG. 22B, the multi-layer catheter tubing 2220 is generally fabricated over a mandrel (not shown). The mandrel is generally axially elongate, round in cross-section and is fabricated from stainless steel with a PTFE outer coating to facilitate removal of the mandrel once the assembly 2220 is completed. The inner layer 2204 is first placed over the mandrel, preferably with a diametric clearance of about 0.001 to 0.005 inches. The reinforcing braid 2222 is next assembled over the inner layer 2204, which is pre-mounted over the mandrel. The braid 2222 can be fabricated using a mechanical braider. The braid 2222 can be compressed in length to allow it to expand diametrically enough to place it over the inner layer 2204. Once in place, the braid can be stretched axially to reduce its diameter to a minimum value. The braid 2222 is next fastened in place at the ends and the outer layer 2206 is slipped over the braid 2222 with sufficient clearance to permit coaxial movement. A length of heat shrink tubing (not shown), generally fabricated from PET or PTFE is next aligned over the outer layer 2206. Using a heat source that surrounds the heat shrink tubing, the heat shrink tubing is heated and reduced in diameter to melt the inner layer 2204 to the outer layer 2206 through the spacing between the windings of the braid 2222. The heat shrink tubing also generates radial inward force distributed sufficiently evenly to coerce the two layers 2204 and 2206 together. Once the heating or welding process is completed, the heat shrink tubing can be cut off or otherwise removed, and the mandrel can be removed leaving the inner lumen 2210 within the composite tubing 2220. The inner layer 2204 and the outer layer 2206 can be fabricated from polymeric materials such as, but not limited to, polyurethane, polyethylene, polypropylene, polyester, Hytrel, silicone elastomer, thermoplastic elastomer, PEEK, polyvinyl chloride, and the like. Materials suitable for use in fabricating the braid 2222 are described elsewhere in this specification for the coil 2108 of FIG. 21. The braid 2222 can comprise between 1 and 32 ends and between 5 and 50 picks per inch. The composite tube 2220 is now configured with the braid 2222 reinforcement sandwiched between two smooth layers 2204, 2206 of polymer. This composite structure 2220 has the benefit of good column strength, good torqueability, excellent kink resistance, and thin wall, all useful features for catheter construction. This composite structure 2220 has higher tensile strength than the coil reinforced structure 2200.

FIG. 23A illustrates a side view of a radially expandable region 2300 comprising a radially expandable mesh 1822 and a length adjustable region 1834 affixed to the distal end of the catheter tubing 2312 within the mesh 1822. The distal end of the radially expandable region 2300 is to the right and the proximal end is to the left in the illustration. The distal end of the length adjustable region 1834 is affixed to a length of tip tubing 2316 which is reinforced with a coil 2314. A guidewire 1610 can be slidably disposed within the coil 2314 and is illustrated protruding out the distal end of the coil 2314. The distal end of the expandable mesh 1822 is affixed to the tip tubing 2316 at the distal attachment joint 2306 while the proximal end of the expandable mesh 1822 is affixed to the tubing 2312 at the proximal attachment joint 2306.

Referring to FIG. 23A, the mesh 1822 can be fabricated from round wire, flat wire, or wire of other cross-sectional shape. The mesh 1822 can be fabricated from metals such as, but not limited to, stainless steel, Nitinol, titanium, tantalum, cobalt nickel alloy, and the like. The mesh 1822 can have spring hardness, any degree of annealing, or it can have shape-memory properties as in the case of Nitinol. The mesh 1822 can further be fabricated from polymeric materials including, but not limited to, polyester (PET), PEN, polyurethane, Hytrel, PEEK, polyimide, polyamide, and the like. The mesh 1822 can further be a composite material with a metal core and a polymeric surround. The mesh 1822 can further be embedded or coated with bioactive agents such as, but not limited to, anti-thrombogenic agents, anti-microbial agents, radioactive particle emitting agents, and the like.

The tip tubing 2316 can serve as a flexible leader tip to permit a catheter to ride along and follow over the guidewire 1610. The tip tubing 2316 can be fabricated from the same polymeric materials as the mesh of FIG. 23A. The coil 2314 can be fabricated from the same metals as those used for the mesh of FIG. 23A. The coil 2314 can further be coated with materials to enhance radiopacity, such materials including, but not limited to, platinum, platinum-iridium, gold, tantalum, and the like. A 50 to 500 micron layer of coating will beneficially improve the radiopacity of the coil 2314. The coil 2314 can have coil spacing ranging from 0 to about 10 wire diameters, and preferably between 0 and 5 wire diameters. The wire used in the coil 2314 can have cross-sectional shapes including, but not limited to, round, oval, rectangular, triangular, and the like. Typical coil 2314 wire diameters can range between 0.001 inches and 0.025 inches, with a preferred range of 0.005 to 0.015 inches. The coil 2314 can also be configured to serve as a distal fixed guidewire permanently affixed to the end of the flow reversal catheter disclosed herein.

FIG. 23B illustrates a side view of a radially expandable region 2320 comprising a radially expandable mesh 2302 at one end of the expandable region 2320, a plurality of struts 2304 at the other end of the expandable region 2320, and a length adjusting region 1834 on the catheter tubing 2312 within the radially expandable region 2320. The distal end of the length adjustable region 1834 is affixed to a length of tip tubing 2316. The proximal end of the struts 2304 are attached to the tubing 2312 at the strut attachment joint 2308 while the distal end of the mesh is affixed to the tip tubing 2316 at the proximal attachment joint 2306. The distal end of the struts 2304 are affixed to the proximal ends of the basket or mesh 1822. The distal end of the coil 2314 is shown protruding out the end of the tip tubing 2316.

Referring to FIG. 23B, the struts can have cross-sectional shapes such as, but not limited to, round, oval, rectangular, triangular, or the like. The struts 2304 can operate like the bars on a moly-bolt wall anchor where axial compression causes the struts 2304 to bend radially outward. In the embodiment of FIG. 23B, axial expansion of the strut ends cause the struts 2304 to reduce in radial or lateral dimension. The struts 2304 can be fabricated with wire, as previously disclosed in this section, they can be created by cutting longitudinal slots (the spaces between the struts) in an axially elongate tube, or they can be created by cutting longitudinal slots in a sheet of material which is rolled into a tube and affixed into the tubular shape with a weld, bond, or other fastening system. The struts 2304 can be configured as wires protruding from the open end of a mesh basket structure 1822.

FIG. 23C illustrates a side view of a radially expandable region 2330 comprising a plurality of struts 2310 that span the entire radially expandable region 2330 and a length adjusting region 1834 on the catheter tubing 2312 within the expandable region 2330. The distal end of the length adjustable region 1834 is affixed to a length of tip tubing 2316. The proximal ends of the struts 2310 are affixed to the tubing 2312 by the strut joint 2308 while the distal ends of the struts 2310 are affixed to the tip tubing 2316 by the strut joint 2308.

Referring to FIG. 23C, the struts 2310 can operate like the bars on a moly-bolt wall anchor where axial compression causes the struts 2310 to bend radially outward. Axial expansion of the strut ends cause the struts 2310 to reduce in radial or lateral dimension. The struts 2310 can be fabricated with wire, as previously disclosed in this section, they can be created by cutting longitudinal slots (the spaces between the struts) in an axially elongate tube, or they can be created by cutting longitudinal slots in a sheet of material which is rolled into a tube and affixed into the tubular shape with a weld, bond, or other fastening system.

FIG. 24A illustrates a side view of a radially expandable region comprising a radially expandable mesh 1822 and a membrane 2402 covering the distal aspect of the mesh 1822.

Referring to FIG. 24A, the membrane 2402 can be affixed to the mesh 1822 or it can be disposed adjacent to the mesh 1822 without being affixed thereto. The membrane 2402 can be positioned inside the mesh 1822, outside the mesh 1822, or formed to envelop and encompass the mesh 1822. The membrane 2402 can be completely liquid and gas impermeable, can be liquid impermeable, or it can be semi-permeable to liquid. Furthermore, the membrane 2402 can be permeable to gas and liquid but impermeable to solid particulates above a given size, for example 10 microns. The membrane 2402 can be fabricated from polymeric materials such as, but not limited to, polyurethane, polyester, PEN, polyimide, polyamide, silicone elastomer, PTFE, FEP, thermoplastic elastomer, or the like. The membrane 2402 can comprise a solid sheet, a woven fabric, a knitted fabric, a braided fabric, or a combination thereof. The membrane 2402 can cover the distal aspect of the mesh, as illustrated. In another embodiment, the membrane 2402 can cover the proximal aspect of the mesh 1822, a central part of the mesh 1822, or it can cover the entire mesh 1822. In an embodiment where the membrane 2402 is positioned on the inside of the mesh 1822, the membrane 2402 can be elastomeric and biased to assume the largest possible unconstrained diameter consistent with the shape of the mesh 1822 in its expanded form, or even larger. In this embodiment, the membrane 2402 can be affixed to the catheter shaft 2316 only, it can be affixed to the mesh 1822 with sliding loops to permit relative motion, or it can be affixed to both the catheter shaft 2316 and the mesh 1822. In an embodiment where the membrane 2402 is positioned outside the mesh 1822, the membrane 2402 can be affixed to the catheter 2316, the distal joint 2306 (as illustrated), the mesh 1822, or a combination of these. Attachments of the membrane 2402 to the mesh 1822 can be advantageously made using loops rather than fixed attachments so that the attachments can move longitudinally on the mesh 1822.

FIG. 24B illustrates a side view of a radially expandable region comprising a radially expandable mesh 2302 at one end of the expandable region, a plurality of struts 2304 at the other end of the expandable region, and a membrane 2404 covering the mesh 2302 on the distal end of the expandable region. The membrane 2404 can have the same characteristics as those described for the embodiments of the mesh 2402 in FIG. 24A.

FIG. 24C illustrates a side view of a radially expandable region comprising a length changing catheter section 1834, a plurality of struts 2310 that span the entire radially expandable region and a membrane 2406 covering the distal end of the struts 2310. The membrane 2406 can have the same characteristics as those described for the embodiments of the mesh 2402 in FIG. 24A.

While embodiments of the present invention have been shown and described, various modifications can be made without departing from the scope of the present invention. The invention, therefore, should not be limited, except to the following claims, and their equivalents.

What is claimed is:

1. A device comprising:
   a catheter having a distal portion, a proximal portion and at least one lumen extending therebetween, the catheter including first and second self-expandable occlusive members disposed over first and second longitudinally expandable portions of the catheter, respectively; and
   a first elongate member insertable through a lumen of the catheter so as to cause expansion of the first longitudinally expandable portion of the catheter and transitioning of the first self-expandable occlusive member from a radially expanded state to a radially collapsed state; and
   a second elongate member insertable through the lumen of the catheter so as to cause expansion of the second longitudinally expandable portion of the catheter and transitioning of the second self-expandable occlusive member from a radially expanded state to a radially collapsed state.

2. A device according to claim 1 wherein the first elongate member is retractable proximally relative to the catheter to cause the first self-expandable occlusive member to transition from the radially collapsed state to the radially expanded state.

3. A device according to claim 1 wherein the second elongate member is retractable proximally relative to the catheter to cause the second self-expandable occlusive member to transition from the radially collapsed state to the radially expanded state.

4. A device according to claim 1 wherein the first and second elongate members each comprise a stylet.

5. A device according to claim 1 wherein the first elongate member comprises an outer pusher tube and the first self-expandable occlusive member comprises a proximal self-expandable occlusive member, and wherein the second elongate member comprises an inner pusher tube and the second expandable occlusive member comprises a distal expandable occlusive member.

6. A method for treating a vessel that is bifurcated into two branches, said method comprising the steps of:
   providing a catheter having first and second self-expandable occlusive members;
   inserting a first elongate member so as to cause the first self-expandable occlusive member to be in a radially collapsed state;
   inserting a second elongate member so as to cause the second self-expandable occlusive member to be in a radially collapsed state;
   inserting the catheter into the vessel such that the first self-expandable occlusive member is distal to a bifurcation of the vessel in one of the branches and the second self-expandable occlusive member is proximal to the bifurcation;

retracting the first elongate member to allow the first self-expandable occlusive member to expand; and retracting the second elongate member to allow the second self-expandable occlusive member to expand.

7. A device comprising:

a catheter having a distal portion, a proximal portion and at least one lumen extending therebetween, the catheter including first and second self-expandable occlusive baskets disposed over first and second longitudinally expandable portions of the catheter, respectively; and a first stylet insertable through a lumen of the catheter so as to cause expansion of the first longitudinally expandable portion of the catheter and transitioning of the first self-expandable occlusive basket from a radially expanded state to a radially collapsed state; and a second stylet insertable through the lumen of the catheter so as to cause expansion of the second longitudinally expandable portion of the catheter and transitioning of the second self-expandable occlusive basket from a radially expanded state to a radially collapsed state.

8. A device according to claim 7 wherein the first stylet is retractable proximally relative to the catheter to cause the first self-expandable occlusive basket to transition from the radially collapsed state to the radially expanded state.

9. A device according to claim 7 wherein the second stylet is retractable proximally relative to the catheter to cause the second self-expandable occlusive basket to transition from the radially collapsed state to the radially expanded state.

10. A device according to claim 7 wherein the first stylet comprises a first tube and the first self-expandable occlusive basket comprises a proximal self-expandable occlusive basket, and wherein the second stylet comprises a second tube disposed within the first tube, insertable from the proximal end of the first tube, and the second expandable occlusive basket comprises a distal expandable occlusive basket.

11. A device comprising:

a catheter having a distal portion, a proximal portion and at least one lumen extending therebetween, the catheter including first and second self-expandable occlusive meshes disposed over first and second longitudinally expandable portions of the catheter, respectively; and a first stylet insertable through a lumen of the catheter so as to cause expansion of the first longitudinally expandable portion of the catheter and transitioning of the first self-expandable occlusive mesh from a radially expanded state to a radially collapsed state; and a second stylet insertable through the lumen of the catheter so as to cause expansion of the second longitudinally expandable portion of the catheter and transitioning of the second self-expandable occlusive mesh from a radially expanded state to a radially collapsed state.

12. A device according to claim 11 wherein the first stylet is retractable proximally relative to the catheter to cause the first self-expandable occlusive mesh to transition from the radially collapsed state to the radially expanded state.

13. A device according to claim 11 wherein the second stylet is retractable proximally relative to the catheter to cause the second self-expandable occlusive mesh to transition from the radially collapsed state to the radially expanded state.

14. A device according to claim 11 wherein the first stylet comprises a first tube and the first self-expandable occlusive mesh comprises a proximal self-expandable occlusive mesh, and wherein the second stylet comprises a second tube disposed within the first tube, insertable from the proximal end of the first tube, and the second expandable occlusive mesh comprises a distal expandable occlusive mesh.

* * * * *